(12) United States Patent
Sachs

(10) Patent No.: US 10,588,670 B2
(45) Date of Patent: Mar. 17, 2020

(54) ANTERIOR SPINAL IMPLANTS FOR REDUCING SPINAL MALALIGNMENT AND ASSOCIATED SYSTEMS AND METHODS

(71) Applicant: MUSC Foundation for Research Development, Charleston, SC (US)

(72) Inventor: Barton L. Sachs, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 16/376,893

(22) Filed: Apr. 5, 2019

(65) Prior Publication Data

US 2019/0298424 A1 Oct. 3, 2019

Related U.S. Application Data

(60) Division of application No. 16/168,106, filed on Oct. 23, 2018, now Pat. No. 10,441,322, which is a (Continued)

(51) Int. Cl.
*A61B 17/56* (2006.01)
*A61B 17/58* (2006.01)
(Continued)

(52) U.S. Cl.
CPC .......... *A61B 17/7059* (2013.01); *A61B 17/70* (2013.01); *A61B 17/86* (2013.01);
(Continued)

(58) Field of Classification Search
CPC combination set(s) only.
See application file for complete search history.

(56) References Cited

U.S. PATENT DOCUMENTS 5,258,031 A 11/1993 Salib et al.
5,380,324 A 1/1995 Muller et al.
(Continued)

FOREIGN PATENT DOCUMENTS

| WO | WO 2007/130699 | 11/2007 |
| WO | WO 2014/127202 | 8/2014 |
| WO | WO 2017/197317 | 11/2017 |

OTHER PUBLICATIONS

U.S. Appl. No. 16/168,106, filed Oct. 23, 2018.

*Primary Examiner* — Sameh R Boles
(74) *Attorney, Agent, or Firm* — Levine Bagade Han LLP

(57) ABSTRACT

Anterior spinal implant devices for reducing spinal malalignment and associated systems and methods are disclosed herein. A spinal implant system configured in accordance with embodiments of the present technology can include, for example, a first vertebral support implanted at an anterior region of a first vertebra of a patient, a second vertebral support implanted at an anterior region of a second vertebra inferior to the first vertebra, and an alignment system configured to be releasably coupled to the first and second vertebral supports. The first and second vertebral supports can extend into and interlock with each other within an interbody space between the first and second vertebrae when the first and second vertebral supports are aligned. The alignment system is configured to reduce angular, vertical, and linear malalignment of the first and second vertebrae relative to each other.

14 Claims, 10 Drawing Sheets

Related U.S. Application Data continuation of application No. PCT/US2017/032494, filed on May 12, 2017.

(60) Provisional application No. 62/336,115, filed on May 13, 2016.

(51) Int. Cl.
  *A61B 17/80* (2006.01)
  *A61F 2/30* (2006.01)
  *A61B 17/70* (2006.01)
  *A61F 2/44* (2006.01)
  *A61B 17/86* (2006.01)
  *A61F 2/46* (2006.01)
  *A61B 17/68* (2006.01)
  *A61F 2/28* (2006.01)

(52) U.S. Cl.
  CPC ............... *A61F 2/44* (2013.01); *A61F 2/447* (2013.01); *A61F 2/4455* (2013.01); *A61F 2/4611* (2013.01); *A61B 2017/564* (2013.01); *A61B 2017/681* (2013.01); *A61F 2002/2835* (2013.01); *A61F 2002/30403* (2013.01); *A61F 2002/30507* (2013.01); *A61F 2002/30517* (2013.01); *A61F 2002/30578* (2013.01); *A61F 2002/30604* (2013.01)

(56) References Cited

U.S. PATENT DOCUMENTS

| | | |
|---|---|---|
| 5,776,197 A | 7/1998 | Rabbe et al. |
| 6,461,359 B1 | 10/2002 | Tribus et al. |
| 6,491,695 B1 | 12/2002 | Roggenbuck |
| 6,610,093 B1 | 8/2003 | Pisharodi |
| 6,613,051 B1 | 9/2003 | Luk et al. |
| 6,663,637 B2 | 12/2003 | Dixon et al. |
| 7,575,600 B2 | 8/2009 | Zucherman et al. |
| 8,430,929 B2 | 4/2013 | Tribus |
| 8,784,492 B2 | 7/2014 | Ferree et al. |
| 8,845,733 B2 | 9/2014 | Oneil et al. |
| 8,932,358 B1 | 1/2015 | Nehls |
| 9,439,691 B2 | 9/2016 | Tribus |
| RE46,371 E | 4/2017 | David et al. |
| 10,441,322 B2 | 10/2019 | Sachs et al. |
| 2005/0277938 A1 | 12/2005 | Parsons |
| 2007/0123989 A1 | 5/2007 | Gfeller et al. |
| 2008/0015694 A1 | 1/2008 | Tribus |
| 2010/0298885 A1 | 11/2010 | Tribus |
| 2012/0239093 A1 | 9/2012 | Moore |
| 2013/0325071 A1* | 12/2013 | Niemiec ............ A61B 17/7059 606/279 |
| 2014/0236300 A1 | 8/2014 | Lowry et al. |
| 2014/0249629 A1 | 9/2014 | Moskowitz et al. |
| 2016/0038306 A1 | 2/2016 | Oneil et al. |
| 2017/0049579 A1 | 2/2017 | Quinlan et al. |
| 2017/0071639 A1 | 3/2017 | Glazer |
| 2019/0053831 A1 | 2/2019 | Sachs et al. |

\* cited by examiner

ANTERIOR SPINAL IMPLANTS FOR REDUCING SPINAL MALALIGNMENT AND ASSOCIATED SYSTEMS AND METHODS

CROSS-REFERENCE TO RELATED APPLICATIONS

This application is a divisional of U.S. patent application Ser. No. 16/168,106 filed Oct. 23, 2018, which is a continuation of International Patent Application Number PCT/US2017/032494 filed May 12, 2017, which claims priority to U.S. Patent Application No. 62/336,115 filed May 13, 2016, the contents of which are incorporated herein by reference in their entirety.

TECHNICAL FIELD

The present technology relates generally to spinal implants and spinal alignment systems. In particular, several embodiments of the present technology are related to anteriorly positioned spinal implants for reducing spinal malalignment, such as spondylolisthesis, and spinal arthrodesis and associated systems and methods.

BACKGROUND

Spondylolisthesis is a condition defined by the anterior displacement of a spinal vertebra or the vertebral column in relation to the inferior vertebrae. It can be caused by isthmic or degenerative conditions. For example, spondylolisthesis can be the result of a congenital abnormality, joint damage from a trauma, a vertebral stress fracture caused by overuse of the joint, and/or joint damage caused by an infection or arthritis. Thus, the condition can affect children, young adults, and older adults alike. The condition, which is often located in the lumbar region of the spine, is separated into five grades depending on the degree of displacement, with Grade 1 referring to the lowest degree of slippage (0-25%) and Grade 5 referring to the highest degree of slippage (over 100%). Symptoms can include back pain, buttock pain, pain that runs from the lower back down one or both legs, difficulty walking, and potentially the loss of bladder or bowel control.

Surgical intervention is used when the pain becomes extreme or there is damage to the nerve root or vertebral column. For example, decompression procedures can remove bone or other tissue to reduce pressure from the vertebral column and/or nerves, and spinal fusion procedures can fuse the vertebrae together to stabilize the spine. Posterior approaches (i.e., accessing from the patient's back) that reduce malalignment and stabilize the spine are typically used to correct high-grade spondylolisthesis. However, the posterior approach makes it difficult to access the pedicles of the vertebrae, in which alignment screws are placed to bring the misaligned vertebrae back into proper alignment. In addition, posterior approaches carry a risk of neurologic injury. For example, studies have shown that 35-40% of posterior surgical reduction procedures resulted in neurologic deficits and complications. Furthermore, posterior approaches require significant disruption of the back muscles and do not allow for the release of the deforming forces from anterior ligaments because they cannot be appropriately accessed from the posterior position. Accordingly, further studies have shown that more than half of patients who underwent surgical posterior fusion treatments for spondylolisthesis had fair or poor results.

Spinal arthrodesis (i.e., spinal fusion) can also be provided from an anterior approach. However, current anterior reduction surgery with interbody fusion has a relatively high chance of failure from loss of reduction (i.e., further slippage) if not combined with a second stage posterior surgery. To address this shortcoming, anterior fusion devices generally require supplemental fixation from the posterior side of the vertebrae. However, supplemental posterior stabilization is susceptible to the disruption of back muscles, neural injury, and difficulty accessing anchor points on the vertebra associated with exclusively posterior approaches.

BRIEF DESCRIPTION OF THE SEVERAL VIEWS OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. The headings provided herein are for convenience only.

DETAILED DESCRIPTION

Figure 1A:
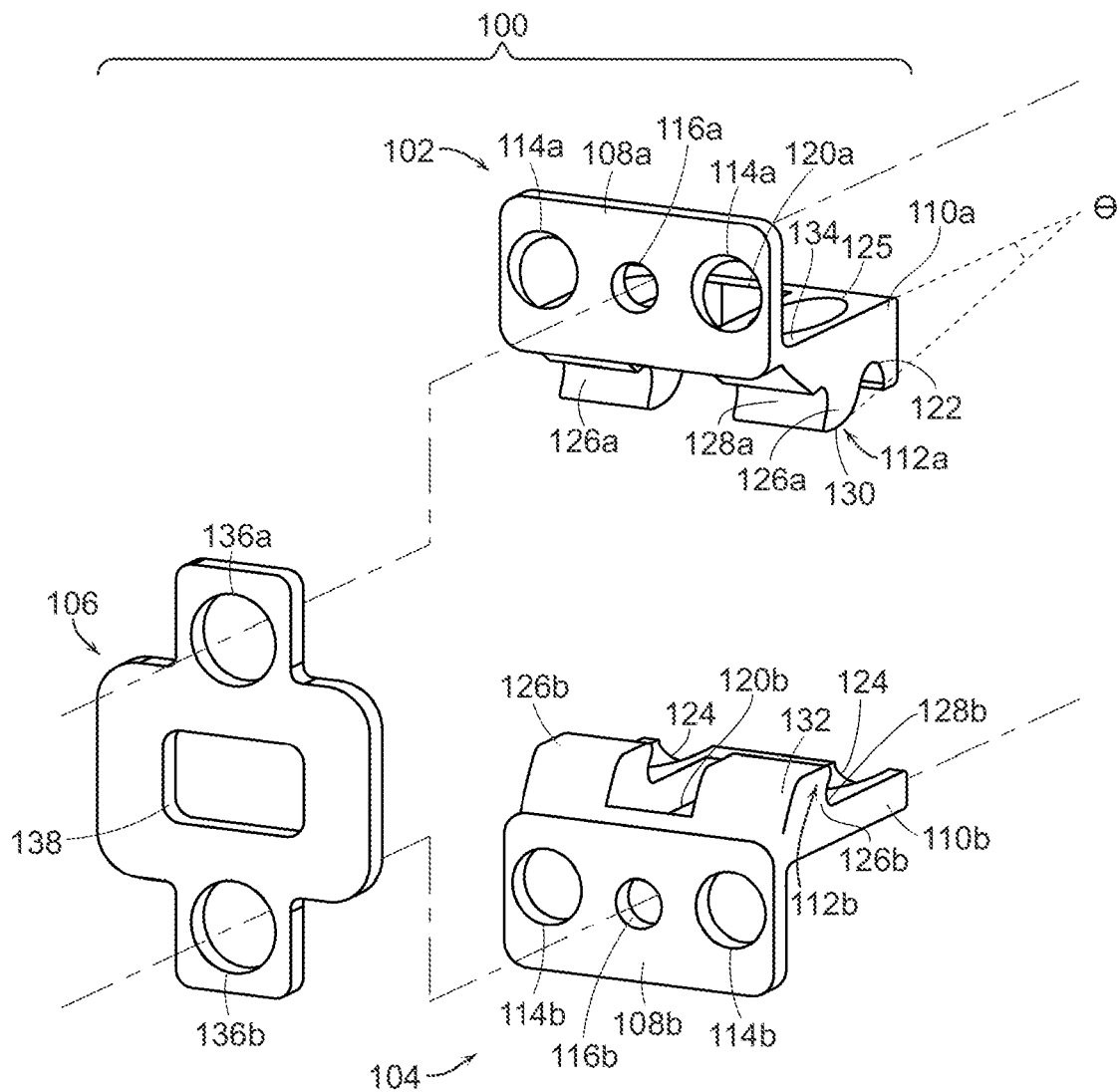
FIG. 1A is an isometric view of a spinal implant device configured in accordance with embodiments of the present technology.

The present technology is generally directed to anterior spinal implants for reducing spinal malalignment and spinal arthrodesis and associated systems and methods. For example, some embodiments of the present technology are directed to integrated spinal implant systems for reducing malalignment and stabilizing the spine. Specific details of several embodiments of the present technology are described herein with reference to FIGS. 1A-8. Although many of the embodiments are described with respect to devices, systems, and methods for reducing the effects of spondylolisthesis in the lumbar region of the spine, other applications and other embodiments in addition to those described herein are within the scope of the present technology. For example, at least some embodiments of the present technology may be useful for correcting spinal malalignment along other portions of the spine, such as the cervical or thoracic spine. In addition, at least some embodiments of the present technology may be useful for correcting spinal malalignment caused by other conditions, such as degenerative disc disease.

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

With regard to the terms "anterior" and "posterior" within this description, unless otherwise specified, the terms can refer to relative positions of portions of a spinal implant device and/or an associated alignment system with reference to the spine or individual vertebra of a patient. For example, when referring to spinal implant systems that align and/or stabilize a spine, "anterior" or "anteriorly" can refer to a position toward the front of a patient's spine or directed toward the front of the patient's body (e.g., toward a forward-facing portion of the body of a vertebra or toward the patient's abdomen), and "posterior" or "posteriorly" can refer to a position toward the back of a patient's spine or directed toward the back of the patient's body (e.g., toward the spinous process of a vertebra).

With regard to the terms "superior" and "inferior" within this description, unless otherwise specified, the terms can refer to relative positions of portions of a spinal implant device and/or an associated alignment system with reference to the spine or individual vertebra of a patient. For example, when referring to spinal implant systems that align and/or stabilize a spine, "superior" or "superiorly" can refer to a position relative to a patient's spine closer to the patient's head (e.g., the L4 vertebra is superior to the L5 vertebra), and "inferior" or "inferiorly" can refer to a position relative to the spine toward the patient's legs.

With regard to the terms "distal" and "proximal" within this description, unless otherwise specified, the terms can reference relative positions of portions of a spinal implant device and/or an associated alignment system with reference to an operator. For example, in referring to an alignment system suitable to deliver and position various spinal implant devices described herein, "proximal" can refer to a position closer to the operator of the alignment system or an incision into the patient (e.g., at the patient's abdominal region), and "distal" can refer to a position that is more distant from the operator of the alignment system or further from the incision.

Figure 1B:
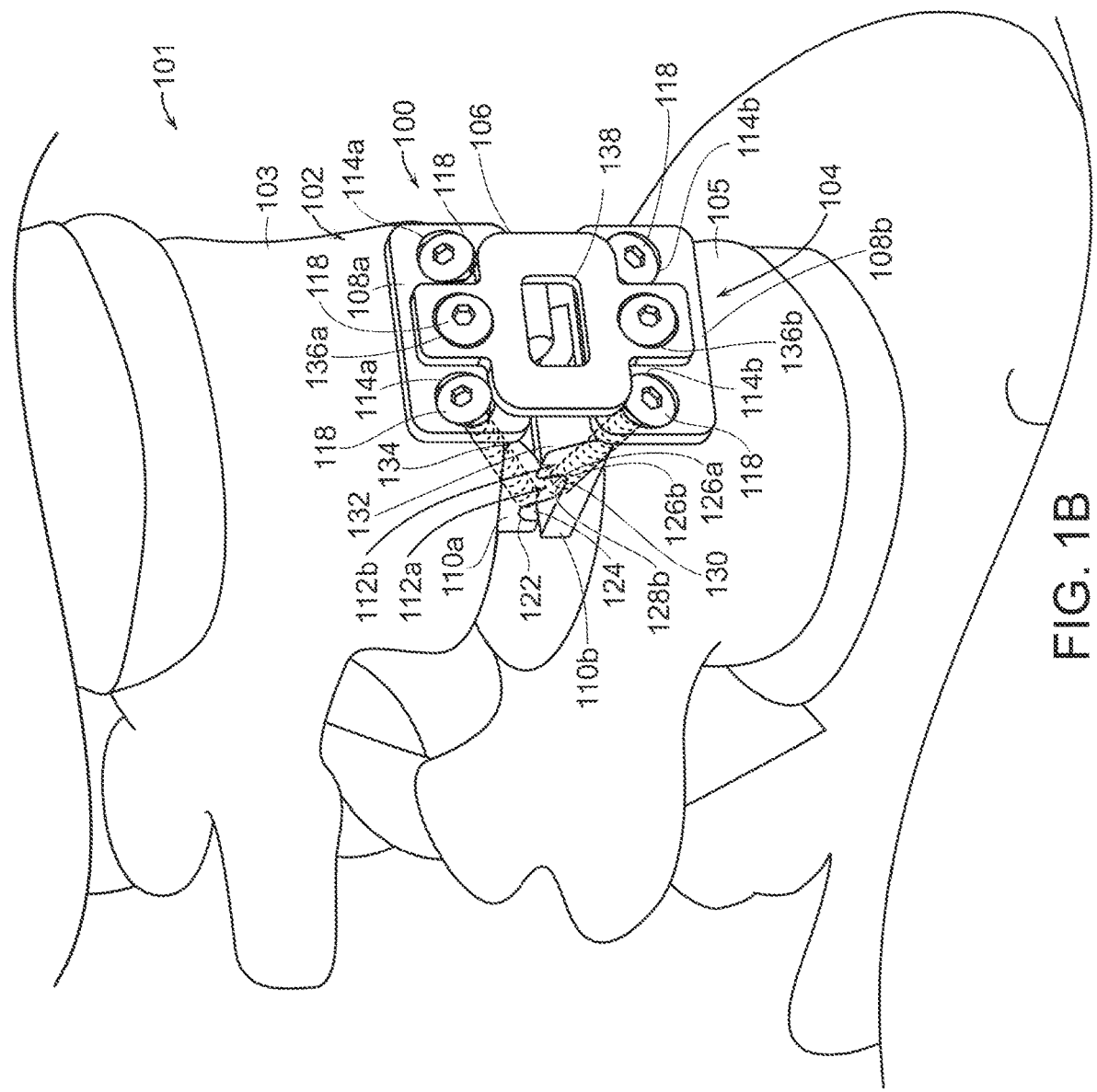
FIG. 1B is an isometric view of the spinal implant device of FIG. 1A implanted in a vertebral column in accordance with embodiments of the present technology.

FIG. 1A is an isometric view of a spinal implant device 100 configured in accordance with embodiments of the present technology, and FIG. 1B is an isometric view of the spinal implant device 100 of FIG. 1A affixed to a vertebral column 101 of a patient in accordance with embodiments of the present technology. The spinal implant device 100 includes a superior or first vertebral support 102 configured to be attached to a superior or first vertebra 103, an inferior or second vertebral support 104 configured to be attached to an inferior or second vertebra 105, and a reinforcement plate 106 extending between and connecting the first and second vertebral supports 102 and 104 (collectively referred to as "vertebral supports 102, 104"). The first vertebral support 102 includes a first anterior portion 108a, a first intervertebral portion 110a extending in a generally transverse manner from the first anterior portion 108a, and a first engagement feature 112a at the first intervertebral portion 110a. Similarly, the second vertebral support 104 includes a second anterior portion 108b, a second intervertebral portion 110b extending in a generally transverse manner from the second anterior portion 108b, and a second engagement feature 112b at the second intervertebral portion 110b. As shown in FIG. 1B, the first and second anterior portions 108a and 108b (referred to collectively as "anterior portions 108") can attach to anterior regions of the corresponding superior and inferior vertebrae 103 and 105, and the first and second intervertebral portions 110a and 110b (referred to collectively as "intervertebral portions 110") extend from the corresponding anterior portions 108 in a posterior direction such that they are position in the intervertebral or interbody space between the superior and inferior vertebrae 103 and 105. When the vertebral supports 102, 104 are correctly aligned relative to each other, the first and second engagement features 112a and 112b (referred to collectively as "engagement features 112") can interlock within the interbody space. The interlocking engagement features 112 and the additional support provided by the anterior plate 106 are expected to maintain and stabilize the first and second vertebrae 103 and 105 relative to each other after a realignment procedure.

As shown in FIGS. 1A and 1B, the anterior portions 108 of the vertebral supports 102, 104 each include at least one vertebral attachment hole or aperture 114 (identified individual as first vertebral attachment holes 114a and second vertebral attachment holes 114b) and at least one plate attachment hole or aperture 116 (identified individually as a first plate attachment hole 116a and a second plate attachment hole 116b). The vertebral attachment holes 114 receive screws 118 that affix the vertebral supports 102, 104 to the corresponding superior and inferior vertebrae 103 and 105, and the plate attachment holes 116 receive screws 118 that affix the anterior plate 106 to the vertebral supports 102, 104 and, optionally, to the adjacent vertebra. For example, the vertebral attachment holes 114 and the plate attachment holes 116 can be configured to receive bone screws having a diameter of 6 mm (0.236 inch). In some embodiments, the vertebral and plate attachment holes 114 and 116 can have other suitable dimensions for receiving screws and/or other fasteners that can attach the vertebral supports 102, 104 to the vertebrae and to the anterior plate 106. As shown in FIGS. 1A and 1B, the anterior portion 108 of each vertebral support 102, 104 can include two vertebral attachment holes 114 (e.g., as shown in FIGS. 1A and 1B) and one plate attachment hole 1 16. In various embodiments, the anterior portions 108 may each include a single vertebral attachment hole 114, more than two vertebral attachment holes 114, more than one plate attachment hole 116, and/or the first anterior portion 108a can include a different number of vertebral and fixation attachment holes 114 and 116 than the second anterior portion 108b. In some embodiments, the vertebral supports 102, 104 can be affixed to the vertebrae using other mechanisms for attaching implants to bone, and/or the anterior plate 106 can be affixed to the vertebral supports 102, 104 using other mechanisms for attaching two portions of an implant together.

As shown in FIG. 1B, the vertebral attachment holes 114 can have an angled surface for receiving the screws 1 18 such that the screws 118 extend into the adjacent vertebral bone at an angle to provide bicortical bone attachment. For example, the first vertebral attachment holes 114a can have an incline angle of about 25°, and the second vertebral attachment holes 114b can have a decline angle of about 25°. When the screws 118 enter the bone at the angle provided by the vertebral attachment holes 114, the screws 118 can extend into or through two portions of the cortical bone: one portion adjacent to the anterior portion 108 of each vertebral support 102, 104 and one portion adjacent to the intervertebral portion 110 of each vertebral support 102, 104. In various embodiments, the vertebral supports 102, 104 can include recesses or apertures in the surfaces of the intervertebral portions 110 facing the associated superior or inferior vertebra to guide the screws 118 into bicortical attachment. For example, as shown in FIG. 1A, a superiorly-facing surface 134 of the first intervertebral portion 110a (i.e., the surface that contacts an inferiorly-facing surface of the superior vertebra 103 (FIG. 1B)) includes at least one aperture or recess 125 sized and shaped to an receive end portion of a screw 118 (FIG. 1B) after the screw 118 passes through a portion of the cortical bone of the superior vertebra 103 proximate to the interbody space. Similarly, the inferiorly-facing surface of the second intervertebral portion 110b can include one or more recesses or apertures (not visible) sized and shaped to receive the end portions of corresponding screws 118 (FIG. 1B) after the screws pass through the cortical bone of the inferior vertebra 105 proximate to the interbody space. This bicortical fixation is expected to enhance the fixation of the vertebral supports 102, 104 to the corresponding vertebra and resist axial forces applied to the screws 118. In some embodiments, the angle of entry provided by the vertebral attachment holes 114 can be larger or smaller to accommodate bicortical bone attachment. In various embodiments, the plate attachment holes 116 can also be configured to receive the screws 1 18 at an angle to provide for bicortical attachment and resist axial forces.

Referring to FIG. 1A, the intervertebral portions 110 of the vertebral supports 102, 104 can also include interbody openings 120 (identified individually as a first interbody opening 120a and a second interbody opening 120b) that extend through the thickness of the intervertebral portions 110. These interbody openings 120 can facilitate subsequent bone fusion between the adjacent vertebrae when bone graft has been inserted into the interbody space during an implantation procedure. In some embodiments, for example, each interbody opening 120 can be about 10 mm in width and 17 mm in length. In various embodiments, the interbody openings 120 can have other suitable dimensions for receiving bone graft and facilitating bone fusion. In some embodiments, each intervertebral portion 110 can have more than one interbody opening 120 and/or other features that facilitate bone fusion. For example, the first vertebral support 102 can include side windows 122 on the lateral sides of the first intervertebral portion 110a to facilitate bone growth through the lateral sides of the implant in addition to axial bone growth. In various embodiments, the second vertebral support 104 can also include side windows similar to those of the first vertebral support 102. In some embodiments, the first vertebral support 102 and/or the second vertebral support 104 include posterior openings 124 extending through posterior regions of the intervertebral portions 110 and configured to facilitate bone growth in a posterior direction from the implant device 100.

As further shown in FIGS. 1A and 1B, the engagement features 112 of the two vertebral supports 102, 104 can be interlocking protrusions or ledges 126 (identified individually as first ledges 126a and second ledges 126b) extending outwardly from the intervertebral portions 110 into the interbody space between adjacent vertebrae. The first engagement feature 112a includes two laterally spaced apart first ledges 126a, and each first ledge 126a includes a first lip surface 128a curved or angled in a generally anterior direction to form a flange. The second engagement features 112b includes two laterally spaced apart second ledges 126b, and each second ledge 126b includes a second lip surface 128b curved or angled in a generally posterior direction to form a recess such that the first and second lip surfaces 128a and 128b (identified collectively as "lip surfaces 128") interface with each other when the first and second vertebral supports 102 and 104 are aligned. For example, each first ledge 126a can have a generally Z-shaped cross-section in which the anteriorly projecting flange of the "Z" engages with the posteriorly directed recess of the corresponding second ledge 126b. The surfaces of the ledges 126 can be filleted or curved as shown in FIGS. 1A and 1B, or they may be defined by straight intersecting surfaces. In some embodiments, the first ledges 126a are formed by intersecting surfaces having an angle less than 90° such that the first ledges 126a can be positioned within and overlap with the corresponding second ledges 126b. For example, the first lip surface 128a and a posterior, inferiorly-facing surface 130 of the first ledge 126a can form an angle of about 50-55°, or the surfaces 128a and 130 can define a different angle relative to each other to mate with the corresponding second ledges 126b. The angled first ledges 126a enhance engagement between the corresponding first and second ledges 126a and 126b and inhibit slippage therebetween, such is when a forward bending moment is applied to the first vertebral support 102 (e.g., caused by the vertebrae attempting to shift during spondylolisthesis relapse). In some embodiments, the lip surfaces 128 and/or the ledges 126 can have other suitable complimentary dimensions. In some embodiments, each vertebral support 102, 104 can include a single ledge 126 (e.g., extending across the width of the intervertebral portion 110) or more than two ledges 126 that interface with a corresponding number of ledges 126 on the opposing vertebral support 102, 104. In various embodiments, the engagement features 112 can have different types of interlocking surfaces and/or different features for affixing the first vertebral support 102 to the second vertebral support 104 when the two vertebral supports 102, 104 are properly aligned.

In some embodiments, the second intervertebral portion 110b of the second vertebral support 104 has an anteriorly-facing surface 132 extending posteriorly in an obtuse angle from the second anterior portion 108b. For example, the second anterior portion 108b and the anteriorly-facing surface 132 can define an angle of 115-135° and/or other suitable obtuse angles. This angled arrangement of the second intervertebral portion 110b can assist in the linear translation (e.g., movement along the posterior-anterior axis, transverse to the axis of the spine 101; also referred to as "horizontal movement") of the first vertebral support 102 relative to the second vertebral support 104. During an alignment procedure, for example, the poster-facing surface(s) of the first vertebral support 102 can glide along the angled anteriorly-facing surface 132 of the second vertebral support 104 as the superior vertebra moves in a posterior direction during linear translation.

The first and second vertebral supports 102 and 104 can be sized and shaped to accommodate the native spinal anatomy to provide proper alignment between adjacent vertebrae. For example, the inwardly surfaces of the first and second vertebrae 103, 105 that attach to intervertebral portions 110 of the vertebral supports 102, 104 are not typically parallel to each other even when properly aligned and, therefore, the spinal implant device 100 can be shaped to accommodate the angle therebetween. For example, the natural angle between the interbody surfaces of the L5 and L4 vertebrae is typically about 8°. Accordingly, the first and second intervertebral portions 110a and 110b can be sized and shaped such that, when the engagement features 112 interlock, the surface of the first intervertebral portion 110a facing the superior vertebra 103 and the surface of the second intervertebral portion 110b facing the inferior vertebra 105 form an angle of about 8° relative to each other. When the spinal implant device 100 is used to realign vertebrae having different natural angles relative to each other, the first and second vertebral supports 102 and 104 can be configured to accommodate the appropriate native angle.

With reference to FIG. 1A, the angled arrangement between the first and second vertebral supports 102 and 104 can be achieved by imparting an angle on the overall structure of first intervertebral portion 110a, while the second intervertebral portion 110b does not have such an angled configuration. For example, the superior-facing surface 134 of the first intervertebral portion 110a (i.e., the surface that contacts an inferiorly-facing surface of the superior vertebra 103 (FIG. 1B)) and the face of the first intervertebral portion 110a that contacts the opposing portions of the second intervertebral portion 110b of the second vertebral support 104 can define an angle Θ relative to each other generally corresponding or related to the angle between the intervertebral portions of the adjacent vertebrae. The overall angle Θ of the first intervertebral portion 110a can be 8°, 10°, 13°, and/or other suitable angles to accommodate the native anatomy. In contrast, the structure of the second intervertebral portion 110b does not have an angle because the inferior-facing surface of the second intervertebral portion 110b and the face of the second intervertebral portion 110b that contacts the opposing portions of the first intervertebral portion 110a are generally parallel. Thus, to accommodate the native anatomy of a patient, the first vertebral support 102 is selected or designed to have an overall angle generally similar to the angle of the native anatomy of the aligned adjacent vertebrae, while the same standard second vertebral support 104 can be used regardless of the angle of the native anatomy. This arrangement of the first and second vertebral supports 102 and 104 allows manufacturers to provide first vertebral supports 102 with different overall structural angles that pair with a single configuration of the second vertebral 104 and, therefore, reduces the total number of parts stored for spinal implant procedures. In various embodiments, the second vertebral support 104, rather than the first vertebral support 102, can be the one to provide the overall angle to the spinal implant device 100, or both the first and second vertebral supports 102 and 104 can have an overall angle that provides the desired angle between the vertebral supports 102, 104.

The vertebral supports 102, 104 can have generally similar dimensions to facilitate delivery to the displaced vertebrae while providing sufficient support to stabilize the vertebrae in the desired position once aligned. For example, the anterior portions 108 can have dimensions to limit the amount of vertebra that needs to be exposed to affix the vertebral supports 102, 104 to the vertebrae. In some embodiments, for example, the anterior portions 108 can extend superiorly or inferiorly along the anterior face of the corresponding vertebra a distance of about 13 mm (0.512 inch), an overall height of 15 mm (0.591 inch), and a mediolateral width of about 28 mm (1.102 inch). The anterior portions 108 can be relatively thin to avoid protruding anteriorly into the abdominal cavity while maintain adequate strength, such as about 2 mm (0.079 inch) in thickness. The intervertebral portions 110 can have a length that facilitates fusion between the superior and inferior vertebrae 103, 105 through the intervertebral space, while not extending so far as to avoid the cauda equina and/or peripheral nerves. For example, the intervertebral portions 110 can have a length (extending posteriorly from the anterior portions 108) of about 22 mm (0.866 inch). In other embodiments, the vertebral supports 102, 104 can have other suitable dimensions based on the patient's anatomy and/or the dimensions required to maintain sufficient support postoperatively.

The vertebral supports 102, 104, as well as the anterior plate 106 can be made from titanium, titanium alloys (e.g., Ti6A14V), cobalt-chrome molybdenum alloys, stainless steel, and/or other medical grade materials suitable for implants in the body. These components can me manufactured using 3-D printing, molding, and/or other suitable manufacturing methods for creating implants.

As discussed above, the anterior plate 106 can extend between the anterior portions 108 of the first and second vertebral supports 102 and 104 to secure the two vertebral supports 102, 104 together when aligned. Accordingly, the anterior plate 106 can have an axial height extending along the entire height of the anterior portions 108 of both the first and second vertebral supports 102 and 104, a mediolateral width that extends along the entire width of the vertebral supports 102, 104, and an overall angle or curvature corresponding to the angle between the first and second vertebral supports 102 and 104. For example, the anterior plate 106 may have an overall height of about 38.384 mm (1.117 inch), a mediolateral width of about 28 mm (1.102 inch), and an overall angle of about 8° in a posterior direction between superior and inferior portions of the anterior plate 106. The anterior plate 106 can also be relatively thin such that the overall thickness of the plate and the anterior portions 108 of the vertebral supports 102, 104 protrude anteriorly only a relatively small distance, such as about 3.5 mm (0.138 inch) in overall thickness. In some embodiments, the anterior plate 106 has a different height, only extends along portions of the first and second anterior portions 108a and 108b of the vertebral supports 102, 104, has a different angle associated with the native spinal anatomy, and/or is made of a sufficiently flexible material and/or includes features (e.g., thinned transverse sections) that allow the anterior plate 106 to bend and flex to accommodate the shape of the vertebral supports 102, 104 relative to each other. The anterior plate 106 includes attachment holes 136 (identified individually as a first attachment hole 136a and a second attachment hole 136b) that align with corresponding plate attachment holes 116 of the first and second vertebral supports 102 and 104 and are configured to receive screws 118 and/or other shafts that secure the anterior plate 106 and the vertebral supports 102, 104 together. The screws 118 that attach the anterior plate 106 to the vertebral supports 102, 104 can be longer than the screws 118 for the vertebral supports 102, 104 to accommodate the additional thickness of the anterior plate 106. For example, the screws 118 can be 25 mm (0.984 inch) in length. In other embodiments, the anterior plate 106 can attach to the vertebral supports 102, 104 using other suitable attachment means.

As further shown in FIGS. 1A and 1B, the anterior plate 106 can include a window 138 that allows a physician (e.g., a surgeon) to place bone graft material into the interbody space to facilitate fusion between the adjacent vertebrae. For example, the window 138 can have dimensions of 8 mm (0.315 inch) in height and 14 mm (0.551 inch) in width. In some embodiments, the window 138 can have larger or smaller dimensions depending upon the sizing of the vertebral supports 102, 104 and/or the native anatomy.

After implantation, the spinal implant device 100 is configured to withstand the forces in vivo to maintain the reduction. That is, the spinal implant device 100 can be configured to maintain 0° of rotation between the adjacent vertebrae and 0 mm of horizontal and vertical translation in vivo. For example, the spinal implant device 100 is expected to withstand 1.99 kN force in the anterior direction to avoid spondylolisthesis relapse, a 6.6 Nm torsion moment, a 15 Nm moment in flexion and extension from fatigue loading, and a 2.4 kN axial load from anatomical loading.

Figure 2:
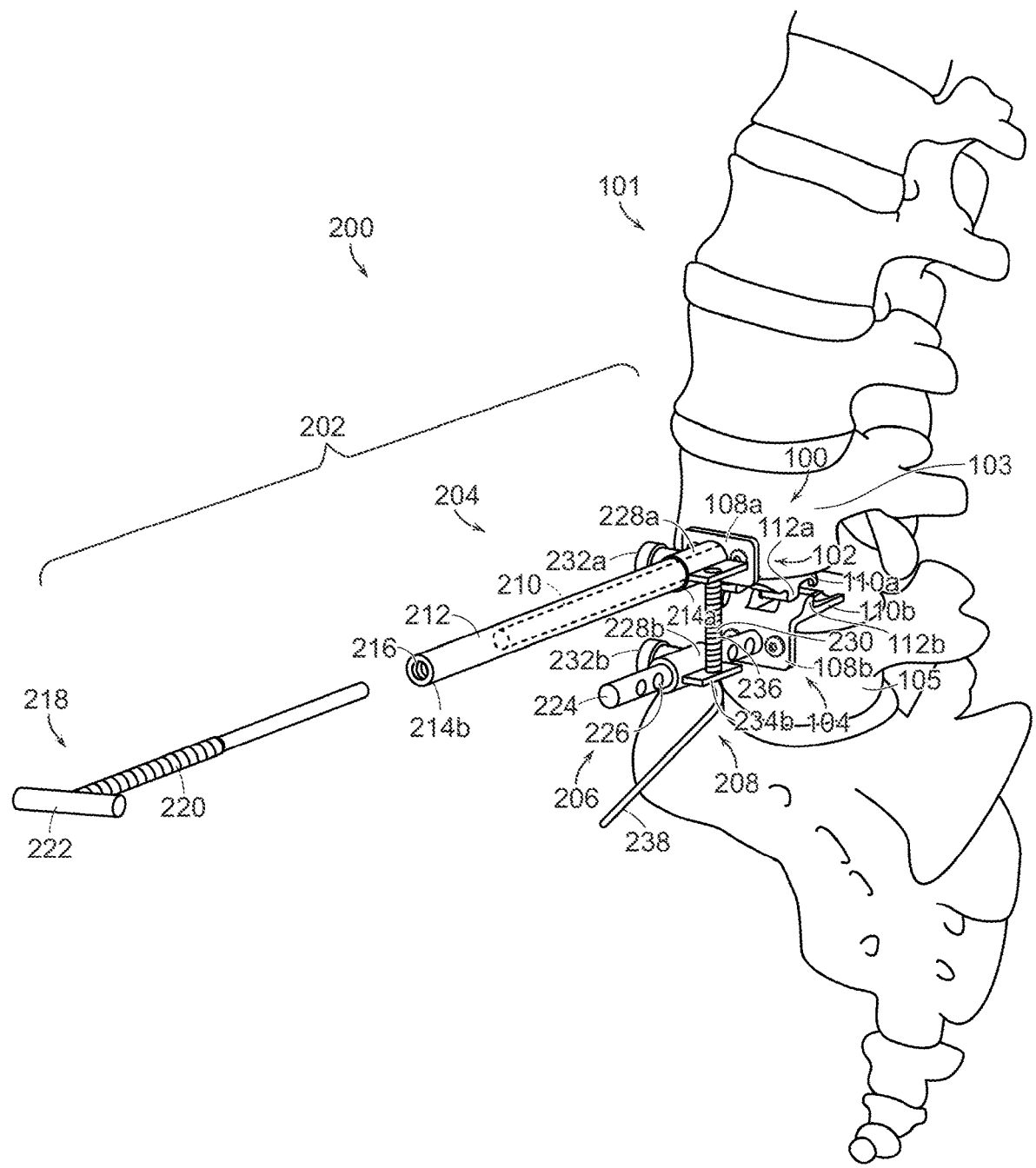
FIG. 2 is an isometric view of portions of a spinal implant system including the spinal implant device of FIG. 1A and an alignment system attached thereto during a spinal implant procedure in accordance with embodiments of the present technology.

FIG. 2 is an isometric view of a spinal implant system 200 including portions of the spinal implant device 100 of FIG. 1A and an alignment system 202 attached thereto during a spinal implant procedure in accordance with embodiments of the present technology. The alignment system 202 includes a superior attachment component 204 that releasably attaches to the first vertebral support 102, an inferior attachment component 206 that releasably attaches to the second vertebral support 104, and a distraction assembly 208 operably coupled to the superior attachment component 204 and the inferior attachment component 206. The components of the alignment system 202 extend in an anterior direction from the vertebral supports 102, 104 such that the alignment system 202 can be attached to the spinal implant device 100 and manipulated from a purely anterior approach. The alignment system 202 is configured to provide angular correction, vertical displacement (i.e., "distraction"), and posterior linear translation of adjacent superior and inferior vertebrae relative to each other to realign the two vertebrae, and thereby allow the first and second vertebral supports 102 and 104 to engage each other to maintain the realigned position of the vertebrae.

As shown in FIG. 2, the superior attachment component 204 is releasably coupled to the first anterior portion 108a of the first vertebral support 102. The superior attachment component 204 can include a superior shaft 210 (shown in broken lines) with a distal end portion that threadably engages the first plate attachment hole 116a of the first vertebral support 102, and a superior tube 212 that extends over the superior shaft 210 and is movable (e.g., slidable) relative to the superior shaft 210. In some embodiments, the superior shaft 210 can include other attachment mechanisms for releasably attaching the superior shaft 210 to the first anterior portion 108a and/or other portions of the first vertebral support 102. The superior tube 212 has a distal end portion 214a configured to be positioned adjacent to the first anterior portion 108a of the first vertebral support 102 and a proximal end portion 214b opposite the distal end portion 214a. The distal end portion 214a of the superior tube 212 can include at least one hole (not visible) that allows for releasable attachment to the distraction assembly 208. The proximal end portion 214b of the superior tube 212 can include an engagement feature 216 that operably couples the superior tube 212 to a linear translation driver 218, which can be used to horizontally displace the superior vertebra 103 relative to the inferior vertebra 105 during an alignment procedure. For example, the engagement features 216 can be internal threads positioned within the proximal end portion 214b of the superior tube 212, and the linear translation driver 218 can include a shaft 220 with a threaded portion that engages the internal threads when rotated within the superior tube 212. As described in further detail below, applying torque to the linear translation driver 218 (e.g., via a handle 222 connected to a proximal portion of the shaft 220) causes a distal end of the shaft 220 of the linear translation driver 218 to press against the proximal end portion of the superior shaft 210 and drive the superior shaft 210 in a posterior direction that, in turn, drives the first vertebral support 102 and the superior vertebrae 103 attached thereto in the posterior direction. In various embodiments, the linear translation driver 218 can be operably coupled to the superior tube 212 using other suitable attachment means and/or may include other mechanisms that drive the first vertebral support 102 in the posterior direction. For example, the linear translation driver 218 can include a piston mechanism to impart posterior linear translation on the superior shaft 210 and the first vertebral support 102 coupled thereto.

The inferior attachment component 206 is releasably coupled to the second anterior portion 108b of the second vertebral support 104. Similar to the superior attachment component 204, the inferior attachment component 206 can include an inferior shaft 224 that threadably engages the second plate attachment hole 116b of the second vertebral support 104. In some embodiments, the inferior shaft 224 can include attachment mechanisms for releasably attaching the inferior shaft 224 to the second anterior portion 108b and/or other portions of the second vertebral support 104. The inferior shaft 224 can also include a plurality of holes 226 extending along its length that allow for attachment to the distraction assembly 208.

The distraction assembly 208 includes a superior distraction component 228a configured to releasably couple to the superior attachment component 204 via a first coupling mechanism 232a, an inferior distraction component 228b configured to releasably couple to the inferior attachment component 206 via a second coupling mechanism 232b, and a distraction member 230 extending between the superior and inferior distraction components 228a and 228b (referred to collectively as "distraction components 228"). In some embodiments, the first and second coupling mechanisms 232a and 232b (referred to collectively as "coupling mechanisms 232") can be plunger connectors that interact with the holes 226 in the inferior shaft 224 and the superior tube 212 to lock the distraction components 228 in place relative to each other. For example, as described in further detail below, the superior distraction components 228a can slide over the superior tube 212 and, when the superior plunger connector aligns with the hole on the distal portion 214a of the superior tube 212, a spring or other biasing member can drive the superior plunger connector into the hole to lock the superior distraction component 228a into place relative to the superior tube 212. Similarly, the inferior distraction component 228b can slide over the inferior shaft 224 with the inferior plunger pulled outwardly (i.e., away from the inferior shaft 224) and, when the inferior distraction component 228b generally aligns the superior distraction component 228a (along an axis extending inferiorly from the superior distraction component 228a), the inferior plunger can be released such that the biasing member drives the inferior plunger connector into the corresponding hole 226 along the inferior shaft 224 to lock the inferior distraction component 228b into place relative to the inferior shaft 224. In other embodiments, the coupling mechanisms 232 can include other suitable attachment mechanisms to attach the distraction components 228 to distal portions of the superior and inferior attachment components 204 and 206, such as threaded engagement features, interfacing surfaces, pressurized attachment mechanisms, and/or interlocking surfaces.

The distraction member 230 operably couples to the superior and inferior distraction components 228a and 228b such that the distraction member 230 can drive the distraction components 228 longitudinally apart from each other along an axis extending through the distraction components 228. In various embodiments, such as the embodiment illustrated in FIG. 2, the distraction member 230 is a threaded shaft or screw 236 that extends through an inferior threaded hole 234b of the inferior distraction component 228b to a superior threaded hole 234a of the superior distraction component 228a. A physician (not shown) can apply torque to the head of the screw 236 (positioned at an inferior side of the inferior distraction component 228b) via a distraction driver 238, such as a hex key (i.e., an "Allen wrench") and/or other type of driver that can engage with and rotate the screw 238. In some embodiments, the distraction member 230 itself includes an integrated component that can be used to rotate the screw 236. Rotating the screw 236 generates a superiorly-directed force that drives the superior distraction component 228a in a superior direction apart from the inferior distraction component 228b (along the axis defined by the screw 236). The superior distraction component 228a acts on the superior attachment component 204, which imparts a superiorly directed force on the first vertebral support 102 and the superior vertebra 103 attached thereto to restore vertebral height between the inferior vertebra 105 and the superior vertebra 103.

In some embodiments, the distraction member 230 can include different mechanisms positioned between the distraction components 228 and configured to vertically translate the distraction components 228 and the vertebrae coupled thereto relative to each other. For example, the distraction member 230 may be a notched shaft that drives the superior distraction component 238a in the superior direction between the notches when driven superiorly by a lever, a piston device that pushes the superior distraction component 238a superiorly, a jack mechanism that drives the superior distraction component 238a in the superior direction when a lever arm is driven in the inferior direction, a pump device that drives the superior distraction component 238a in the superior direction when an actuator is squeezed, a hydraulically-activated driver that drives the superior distraction component 238a in the superior direction when fluid is delivered between the distraction components 228, and/or other suitable components to distract the superior vertebra 103 from the inferior vertebra 105.

In operation, the spinal implant system 200 can realign and stabilize vertebral segments to treat spondylolisthesis and/or other spinal malalignment by correcting forward displacement and sagittal rotation deformities, as well as distract adjacent vertebrae to restore intervertebral height. The first vertebral support 102 can be attached to the displaced superior vertebrae 103, and the second vertebral support 104 can be attached to the vertebra 105 immediately inferior to the displaced vertebra 103. For example, lumbar spondylolisthesis often occurs when the L4 vertebra slips anteriorly over the L5 vertebra, and therefore the first and second vertebral supports 102 and 104 can be attached to the L4 and L5 vertebrae, respectively. The superior attachment component 204 can then be attached to the first vertebral support 102 and the inferior attachment component 206 can be attached to the second vertebral support 104. A physician can apply torque to the superior attachment component 204, such as the superior tube 212, to correct the angle of the superior vertebra 103 caused by the deformity. For example, the superior attachment component 204 can be configured to withstand at least 13.75 Nm of torque and adjust the sagittal rotation by at least 30°.

When the distraction assembly 208 is operably coupled to the superior and inferior attachment components 204 and 206, the physician can manipulate the distraction member 230 (e.g., by rotating to the distraction screw 236) to distract the superior and inferior vertebrae 103 and 105. For example, the distraction assembly 208 can displace the superior and inferior distraction components 228 (and the vertebrae 103, 105 attached thereto) by a height of at least 11.2 mm, and the spinal implant system 200 can be configured to withstand at least 422 N of force in the superior direction to provide the desired distraction. With the vertebrae 103, 105 vertically spaced apart from each other, the physician can manipulate the linear translation driver 218 (e.g., rotate the linear translation shaft 220) to move the superior vertebra 103 in a posterior direction back into alignment with the inferior vertebra 105 such that the engagement features 112 lock into place in the interbody space between the vertebrae 103, 105. For example, the linear translation driver 218 and the components coupled thereto can linearly translate the superior vertebrae 103 a distance of at least 46.3 mm and withstand a force of at least 1.99 kN to do so. With the engagement features 112 interlocked, the physician can remove the alignment system 202 from the vertebral supports 102, 104, and secure the anterior plate 106 (FIGS. 1A and 1B) to vertebral supports 102, 104 to reinforce and stabilize the corrected vertebral position. In some embodiments, the components of the spinal implant system 200 can be configured to provide larger or smaller degrees of angular correction, larger or smaller vertical displacement, and/or larger or smaller linear displacement, and/or the spinal implant system 200 can be configured to withstand greater or smaller forces to provide the desired alignment. In various embodiments, the spinal implant system 200 can be used for only angular correction, distraction, or linear alignment depending on the spinal deformity.

The spinal implant system 200 is expected to provide an integrated system for realigning and stabilizing vertebrae using an anterior approach and anterior fixation. In various embodiments, for example, the spinal implant system 200 can correct Grade I-V spondylolisthesis deformities from the anterior side of the spine. This purely anterior approach and stabilization is not subject to the neurologic complications and disruption of back muscles associated with systems that rely on posterior access and/or posterior fixation. Further, the anterior approach allows the physician to directly visualize the herniated disc, tightened ligaments, and/or other reactive anatomical changes that occur in an attempt to stabilize the spine or as a result of the misaligned vertebrae. Accordingly, the physician can readily perform a discectomy and/or release the tightened anatomical structures (e.g., the anterior longitudinal ligament) from the anterior position before or during an alignment and implantation procedure. After correcting the spinal malalignment and restoring trunk height with the alignment system 202, the spinal implant device 100 is expected to provide standalone anterior fixation for Grade I-V spondylolisthesis deformities to maintain the vertebral alignment without the need for supplemental posterior fixation. Further, the sizing of the vertebral supports 102, 104 and the anterior plate 106 (FIGS. 1A and 1B) have a small mediolateral width relative to other spinal implants and, therefore, require a smaller incision and less exposed vertebral space for implantation. The spinal implant device 100 is also expected to leave significant surface area of the vertebrae in the interbody space exposed (e.g., via the intervertebral openings 120, side windows 122, and posterior openings shown in FIG. 1A) and, therefore, facilitates high fusion rates between the adjacent vertebrae and enhance vertebral stabilization postoperatively. In addition, the alignment system 202 is configured such that all the forces necessary to realign displaced vertebrae and restore trunk height can be provided manually and without substantial strain on the physician. For example, the superior attachment component 204 provides a lever arm that increases the moment on the vertebra for angular correction, and the threads of the distraction assembly 208 and the linear translation driver 218 can overcome deforming forces for distraction and linear translation.

Furthermore, the spinal implant system 200 has modular components that can be assembled within the patient during a surgical procedure, which is expected to provide flexibility based on the constraints on the native anatomy. For example, the modular spinal implant device 100 can be assembled and locked together within the patient. Differently shaped or sized vertebral supports 102, 104 and/or components of the alignment system 202 can also be selected intraoperatively to appropriately align and stabilize the spine. In various embodiments, portions of the spinal implant system 200 can be preassembled before implantation and/or alignment to expedite the procedure. For example, the first vertebral support 102 can be attached to the superior attachment component 204 and/or portions thereof before implantation of the first vertebral support 102, the second vertebral support 104 can be attached to the inferior attachment component 206 and/or portions thereof before implantation of the second vertebral support 104, the superior and inferior distraction components 228a and 228b can be pre-attached to the distraction member 230 before attaching them to the superior and inferior attachment components 204 and 206, the inferior distraction component 228b can be pre-attached to the distraction member 230 before connecting the inferior distraction component 228b to the inferior shaft 224, and/or other portions of the spinal implant system 200 can be preassembled.

Figure 3:
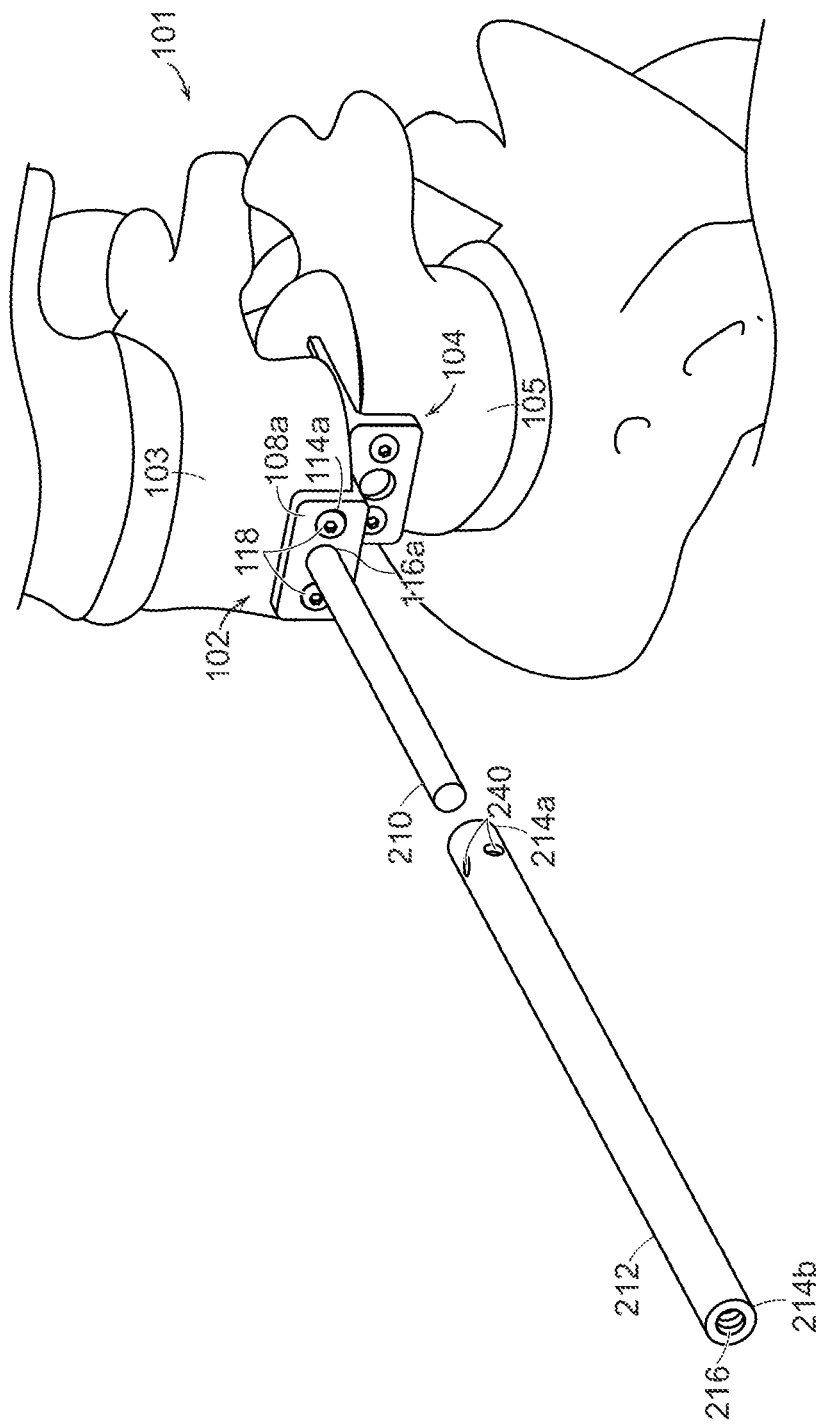
FIG. 3 is an isometric view of portions of the spinal implant device and the alignment system of FIGS. 1A-2 during a stage of a spinal realignment and stabilization procedure in accordance with embodiments of the present technology.

FIGS. 3-8 illustrate various stages of a realignment and stabilization procedure using the spinal implant system 200 described above. For example, FIG. 3 is an isometric view of portions of the spinal implant device 100 and the alignment system 202 during a stage of the realignment and stabilization procedure in accordance with embodiments of the present technology. To begin the realignment and stabilization procedure, a physician first makes an incision in a patient's abdomen, side, or other location anterior to the patient's vertebral column 101 to access and expose anterior portions of the misaligned vertebrae. This can be done using a retroperitoneal or transperitoneal approach. The incision can be relatively short in length and the and the exposed portions of the vertebrae can be relatively short in height because the first and second vertebral supports 102 and 104 can be delivered and attached separately and are designed such that the anterior portions 108 only extend along a portion of the overall height of the vertebrae. For example, the faces of the anterior portions 108 may be configured such that they do not extend past the midpoint of the height of the average L5 vertebra of an adult male (e.g., about 13 mm (0.512 inch)). Unlike posterior approaches, from the anterior vantage point, the physician can directly visualize the reactive anatomical structures holding the deformity, and can delicately release those reactive structures surrounding the displaced vertebrae (e.g., by cutting or otherwise releasing ligaments). The physician can also perform a discectomy to remove the herniated disc material presses on a nerve root or spinal cord between the misaligned vertebrae, which is aided by the anterior visualization of the disc space.

After the vertebral space is adequately exposed and the desired structures released or removed, the physician can affix the first vertebral support 102 to the superior vertebra 103 along the mediolateral midline of the vertebral body using the screws 118 that pass through the lateral first holes 114a on the first anterior portion 108a of the first vertebral support 102. The screws 118 can be angled in an inferior direction such that they pass through two portions of the cortical bone of the superior vertebra 103 to enhance fixation. The physician can also affix the second vertebral support 104 to the inferior vertebra 105 along the mediolateral midline of the vertebral body using the screws 118 that are angled in a superior direction through the lateral second holes 114b on the second anterior portion 108b of the second vertebral support 104 to provide bicortical fixation of the second vertebral support 104. In some embodiments, the screws 118 are not angled superiorly or inferiorly and/or do not provide bicortical fixation. In various embodiments, the second vertebral support 104 may be affixed to the inferior vertebra 105 during a subsequent stage of the procedure, such as after angular correction of the superior vertebra 103.

After the first vertebral support 102 has been attached to the superior vertebra 103, the superior shaft 210 can be releasably attached (e.g., via threaded engagement with the first plate attachment hole 116a) to the first vertebral support 102. The superior tube 212 can then slide over the superior shaft 210. As shown in FIG. 3, the distal end portion 214a of the superior shaft 210 can include a plurality of holes 240 positioned around its circumference, which can be configured to interface with the subsequently attached superior distraction component 228a (FIG. 2).

Figure 4:
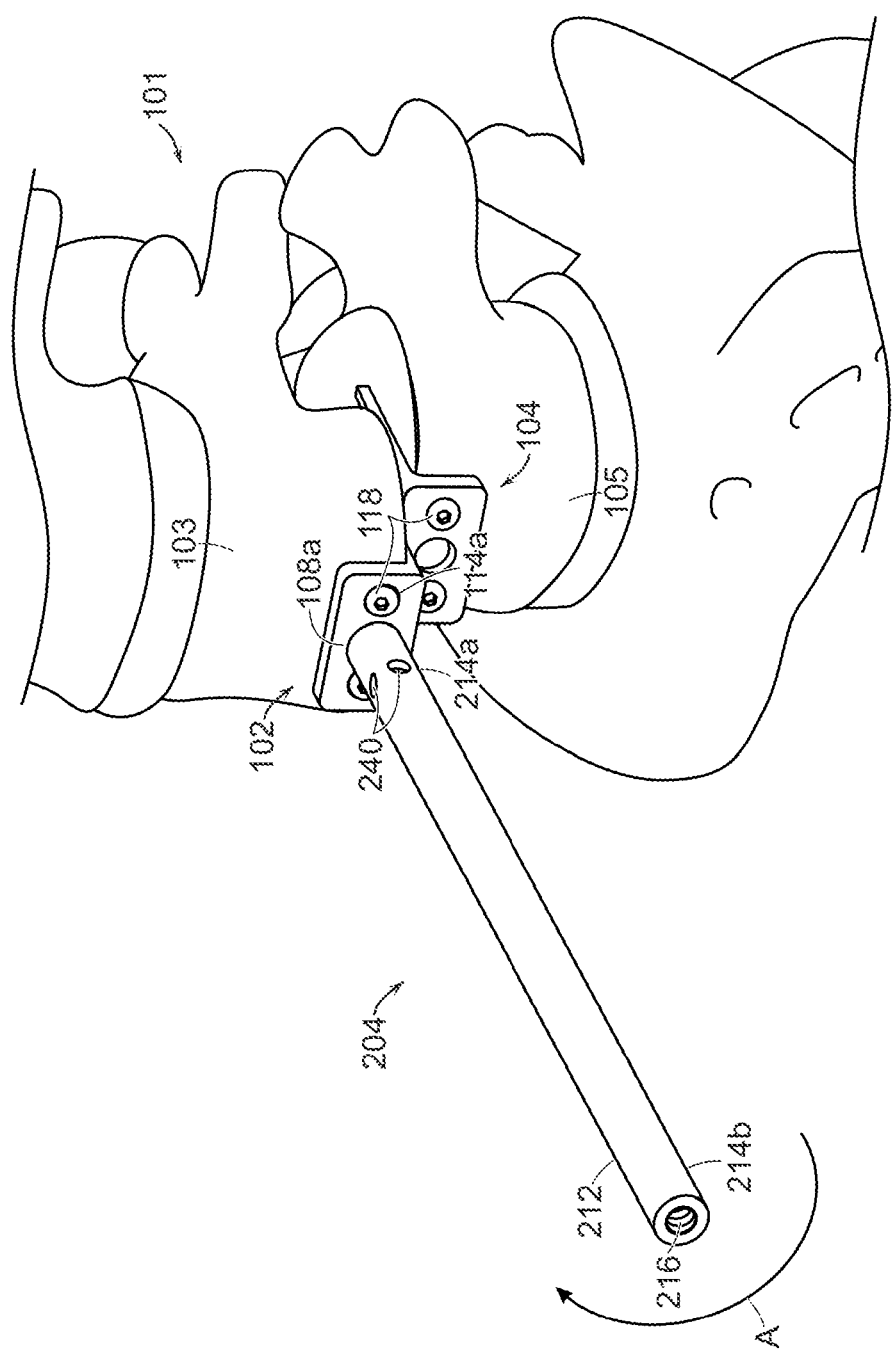
FIG. 4 is an isometric view of portions of the spinal implant device and the alignment system of FIGS. 1A-2 during an angular correction stage of the spinal realignment and stabilization procedure in accordance with embodiments of the present technology.

As shown in FIG. 4, once the superior tube 212 is in place, the physician can apply torque to the superior tube 212 (as indicated by arrow A) to correct the angle of the superior vertebra 103. The superior tube 212 serves as a lever arm to provide a greater mechanical advantage to the physician while correcting the angle of the displaced vertebra 103.

Figure 5A:
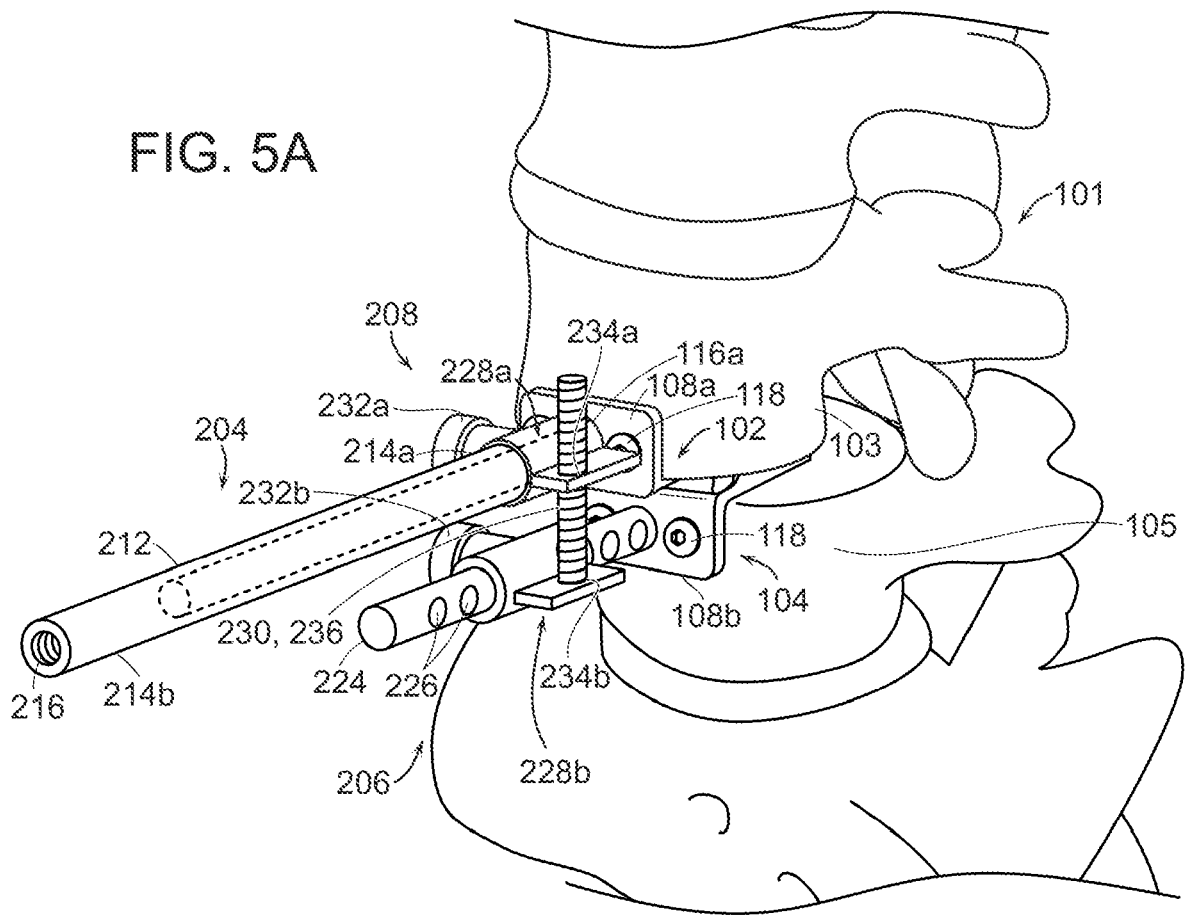
FIG. 5A is an isometric view of portions of the spinal implant device and the alignment system of FIGS. 1A-2 during an intermediate attachment stage of the spinal realignment and stabilization procedure in accordance with embodiments of the present technology.

FIG. 5A is an isometric view of a subsequent stage of the spinal realignment and stabilization procedure in accordance with embodiments of the present technology. At this stage, the inferior shaft 224 of the inferior attachment component 206 is releasably attached (e.g., via threaded engagement with the second plate attachment hole 116b) to the second vertebral support 104. In various embodiments, the inferior shaft 224 can act as a lever arm to adjust the angle of the inferior vertebra 105 in a similar manner as the superior attachment component 204.

The distraction assembly 208 can then be coupled to the superior and inferior attachment components 204 and 206. The physician can slide the superior distraction component 228a over the superior tube 212, and slide the inferior distraction component 228b over the inferior shaft 224. The superior distraction component 228a is locked in position along the superior tube 212 via the first coupling mechanism 232a. When the first coupling mechanism 232a is a plunger connector (e.g., as shown in FIG. 5A), the physician can pull a plunger cap outwardly as the superior distraction component 228a slides along the superior tube 212 until the superior distraction component 228a aligns with one of the holes 240 (FIGS. 3 and 4) in the superior tube 212. At this time, the physician can then release the plunger cap, which drives the plunger into the hole 240 to lock the superior distraction component 228a in place. The inferior distraction component 228b can be locked to the inferior attachment component 206 in a similar manner.

Figure 5B:
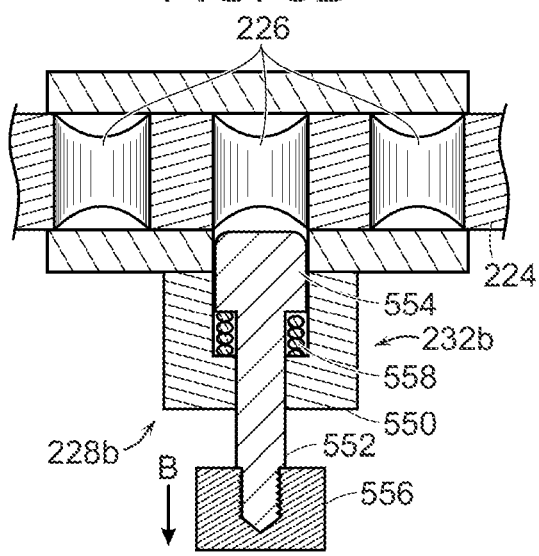
FIGS. 5B and 5C are top cross-sectional views of a portion of a distraction assembly of the alignment system of FIG. 5A shown before and after engagement with a shaft of the alignment system, respectively, in accordance with embodiments of the present technology.
Figure 5C:
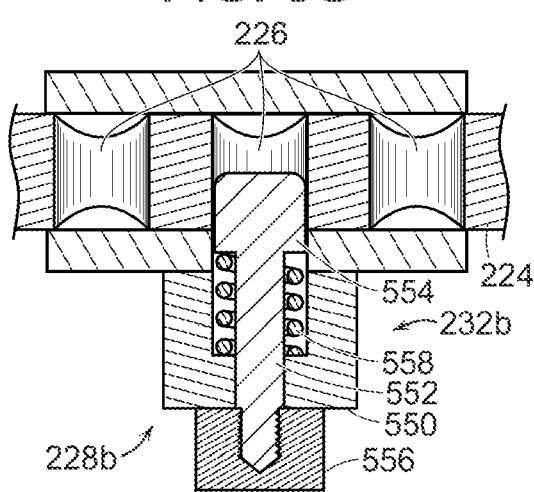

FIGS. 5B and 5C, for example, are top cross-sectional views illustrating additional detail of the inferior distraction component 228b with the second coupling mechanism 232b before and after engagement with the inferior shaft 224, respectively, in accordance with embodiments of the present technology. The second coupling mechanism 232b can include a plunger housing 550, a plunger 552 having a head portion 554 positioned within the plunger housing 550 in a non-engaged state (FIG. 5B), a plunger cap 556 operably coupled to the plunger 552 and accessible to the physician, and a spring 558 acting on the head portion 554 of the plunger 552. In operation, the physician can pull the plunger cap 556 outwardly from the plunger housing 550 (in the direction of arrow B) while the inferior distraction component 228b slides along the inferior shaft 224 (FIG. 5B). Once the second coupling mechanism 232b is aligned with the desired hole 226 along the inferior shaft 224 (e.g., when the superior and inferior distraction components 228a and 228b are generally aligned), the physician can release the plunger cap 556. As shown in FIG. 5C, this allows the spring 558 to decompress and act on the head portion 554 of the plunger 552 to drive the plunger 552 into the adjacent hole 226 of the inferior shaft 224, thereby locking the inferior distraction component 228b in place. The first coupling mechanism 232a can operate in a similar manner as the second coupling mechanism 232b shown in FIGS. 5B and 5C. In some embodiments, the distraction components 228 can be secured to the superior and inferior attachment components 204 and 206 using other suitable means.

With the superior and inferior distraction components 228a and 228b locked in place, the distraction member 230 can be coupled between the distraction components 228. As shown in FIG. 5A, for example, the distraction screw 236 can be threaded through the inferior threaded hole 234b of the inferior distraction component 228b and then threaded through the superior threaded hole 234a of the superior distraction component 228a. In some embodiments, the distraction member 230 can be pre-attached to the inferior distraction component 228b before the inferior distraction component 228b is attached to the inferior attachment component 206.

Figure 6:
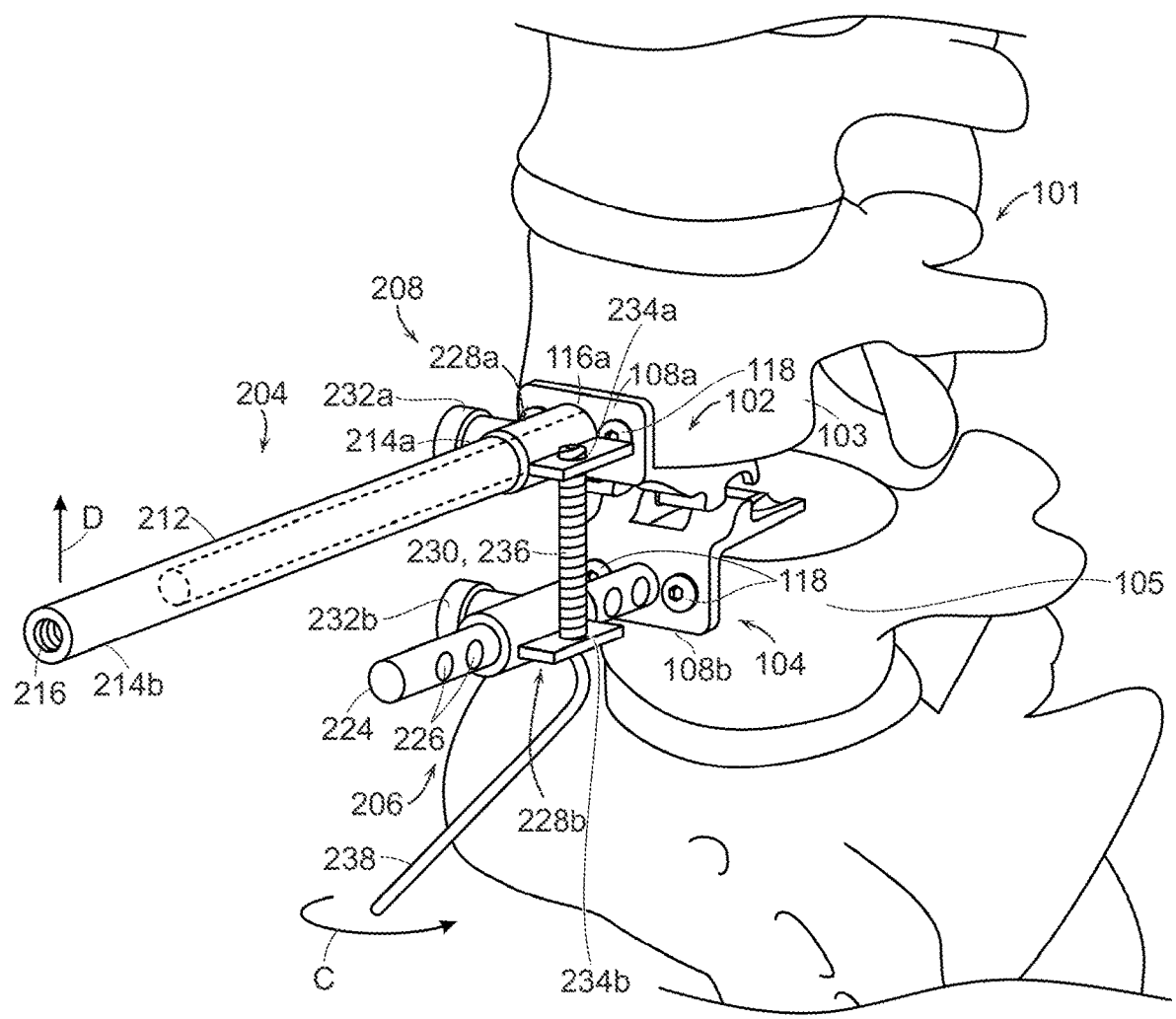
FIG. 6 is an isometric view of portions of the spinal implant device and the alignment system of FIGS. 1A-2 during a distraction stage of the spinal realignment and stabilization procedure in accordance with embodiments of the present technology.

As shown in FIG. 6, once the distraction assembly 208 is in place, the physician can insert the distraction driver 238 (e.g., a hex key) into the head of the distraction screw 236 and apply torque to the distraction driver 238 (as indicated by arrow C). This spins the distraction screw 236, which translates the superior distraction component 228a and the superior vertebra 103 coupled thereto in the superior direction (as indicated by arrow D) to correct intervertebral height. That is, the distraction assembly 208 can drive the superior vertebra 103 superiorly to space the superior and inferior vertebra 103 and 105 vertically apart from each other. This spacing restores the trunk height of the vertebral column 101 and allows for subsequent linear translation of the vertebrae 103, 105 relative to each other along the posterior-anterior axis. In addition, the anterior distraction of the vertebrae 103, 105 opens up the space between the two vertebrae 103, 105 in manner that protects the adjacent nerves (e.g., the L5 nerve) rather than stretching or compressing the nerve as often occurs with posterior approaches. In some embodiments, the distraction screw 236 is manipulated from the opposite side as shown in FIG. 6 (i.e., from a position proximate to the superior distraction component 228a). In various embodiments, the distraction member 230 and/or the distraction driver 238 can be something other than a screw and wrench that vertically translate the adjacent vertebrae relative to each other, such as a jack mechanism, a piston, a pump, and/or other suitable devices.

Figure 7A:
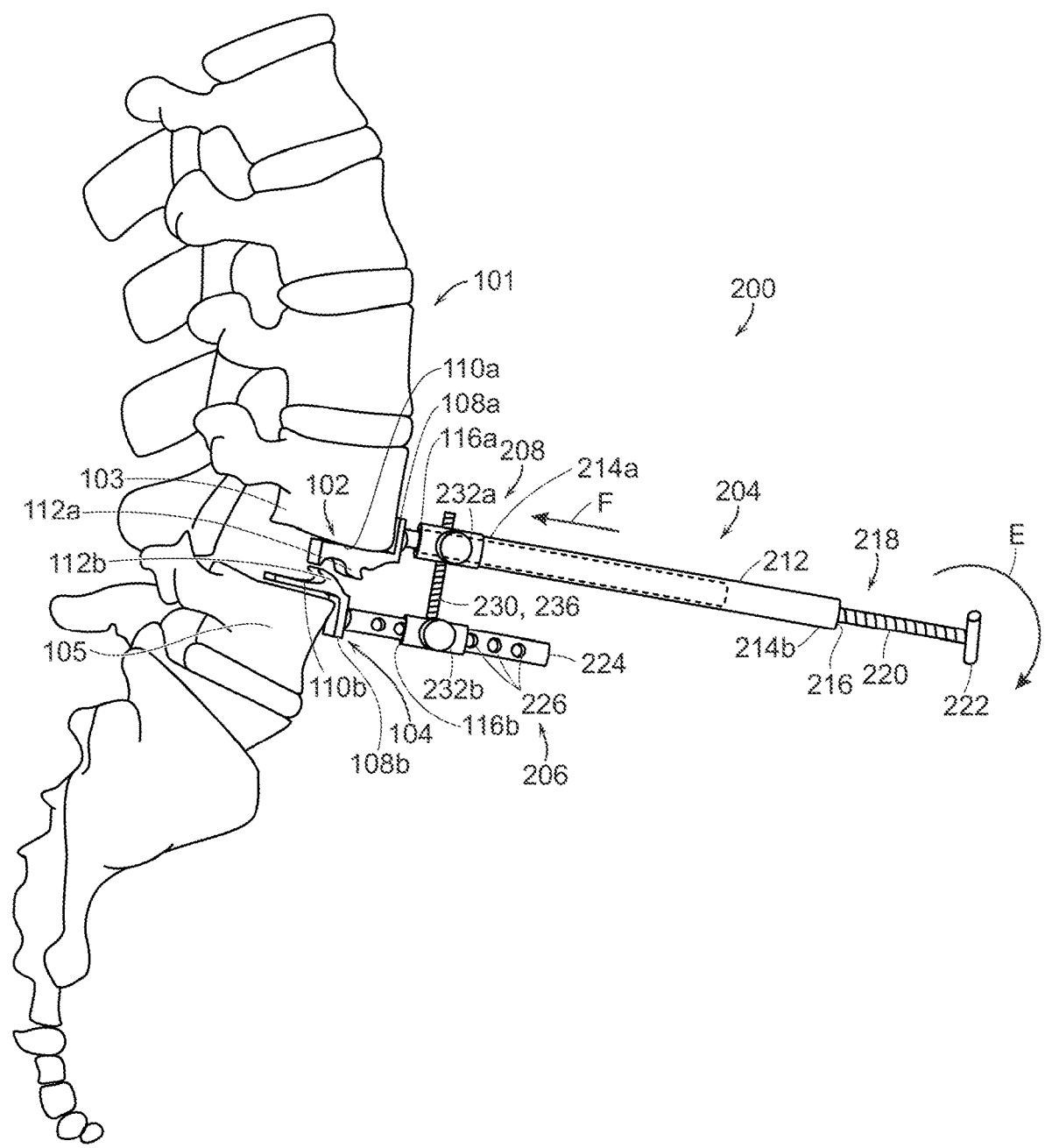
FIG. 7A is an isometric view of portions of the spinal implant device and the alignment system of FIGS. 1A-2 during a linear translation stage of the spinal realignment and stabilization procedure in accordance with embodiments of the present technology.

Once intervertebral height has been restored, the spinal implant system 200 can be used to linearly translate the adjacent vertebrae 103, 105. FIG. 7A, for example, is an isometric view of the spinal implant system 200 during a linear translation stage of the spinal realignment and stabilization procedure in accordance with embodiments of the present technology. During linear translation, the linear translation driver 218 is attached to the superior tube 212 by inserting the linear translation driver 218 into the superior shaft 210 and threading the threaded shaft 220 into engagement with internal threads 216 (FIGS. 2-5A) of the superior tube 212. Torque is applied to the linear translation driver 218 via the T-handle 222 (as indicated by arrow E) rotate the linear translation driver 218 further into the superior tube 212. This causes the distal end of the linear translation driver 218 to apply force against the superior shaft 210 (FIGS. 2 and 3) within the superior tube 212, which in turn transmits a force to the first vertebral support 102 and the superior vertebra 103 attached thereto (as indicated by arrow F), driving the first vertebral support 102 and the superior vertebra 103 in a posterior direction.

Figure 7B:
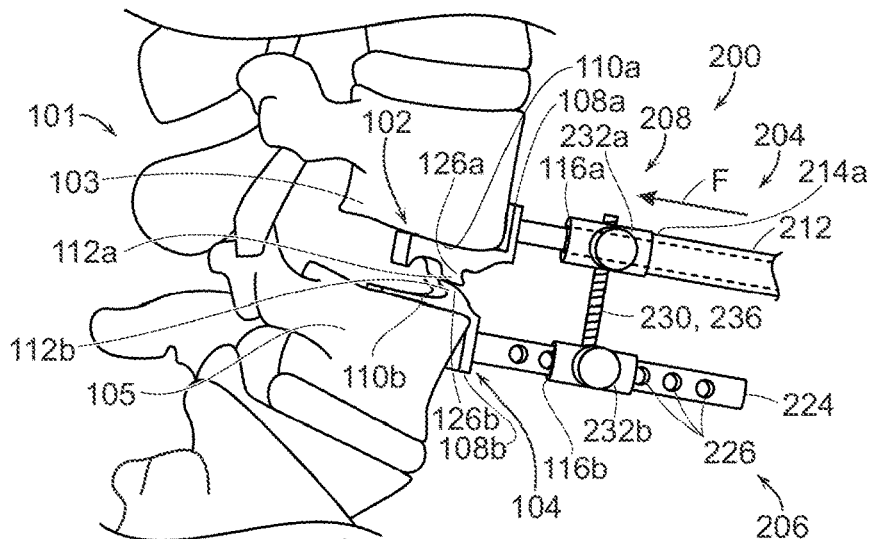
FIGS. 7B-7D are enlarged isometric views of the spinal implant device and the alignment system of FIG. 7A during various stages of linear translation and distraction of the spinal realignment and stabilization procedure in accordance with embodiments of the present technology.
Figure 7C:
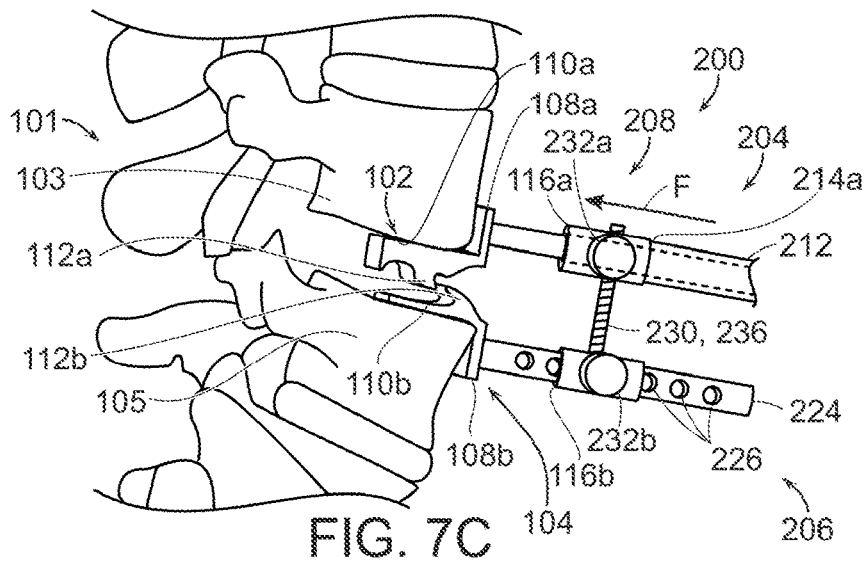
Figure 7D:
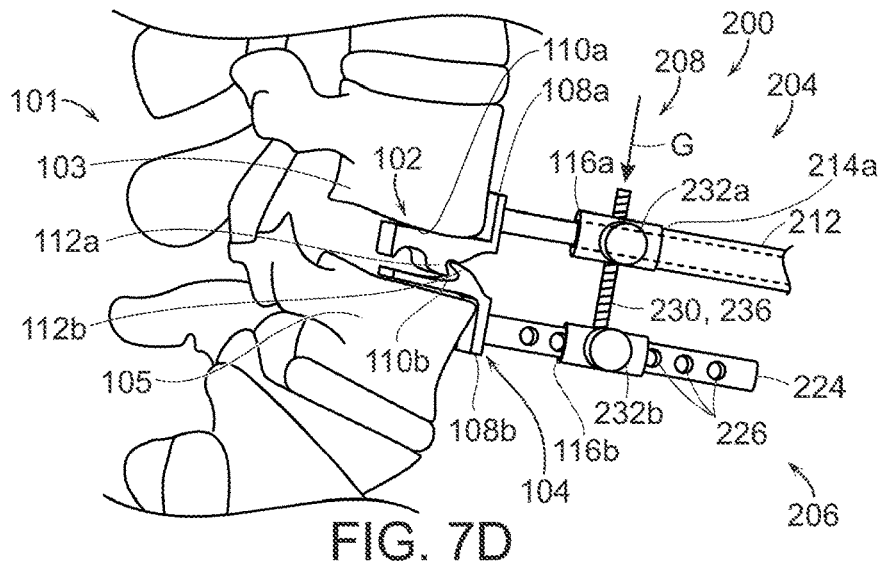

FIGS. 7B-7D are enlarged isometric views of the spinal implant device 100 and the alignment system 202 of FIG. 7A illustrating various stages of linear translation and distraction. As shown in FIGS. 7B and 7C, as the vertebral column 101 moves posteriorly, the first vertebral support 102 moves posteriorly in relation to the second vertebral support 104. More specifically, the force (indicated by arrow F) drives the first ledges 126a of the first engagement feature 112a of the first vertebral support 102 posteriorly past the second ledges 126b of the second engagement feature 112b of the second vertebral support 104. As shown in FIG. 7D, once the first ledges 126a are appropriately aligned with the second ledges 126b, the physician can lower the first vertebral support 102 to make contact with the inwardly-facing lower surface of the second vertebral support 104 and engage the ledges 126 by adjusting the distraction height via the distraction assembly 208 (e.g., via the distraction driver 238 of FIG. 6). In some embodiments, the engagement features 112 of the two vertebral supports 102, 104 can automatically engage when linearly aligned without adjusting the distraction height.

In various embodiments, the inferior attachment component 206 can include a shaft and tube configuration similar to the superior shaft 210 and the superior tube 212 to facilitate angular adjustments of the inferior vertebra 105 and/or allow for linear translation of the inferior vertebra 105 (e.g., if the vertebra was displaced in a posterior direction). In some embodiments, the inferior attachment component 206 can include a shaft and tube configuration while the superior attachment component 204 includes a shaft similar to that of the inferior shaft 224. In this embodiment, the inferior attachment component 206 can be used to provide angular correction and linear displacement of the inferior vertebra.

Once the two vertebral supports 102, 104 are in the proper position and the engagement features 112 are engaged with each other, the physician can remove the instruments of the alignment system 202 from the first and second vertebral supports 102 and 104. For example, the physician can remove the distraction assembly 208, the superior attachment component 204, and the inferior detachment component 206 sequentially as individual components or simultaneously with two or more components still attached to each other.

Figure 8:
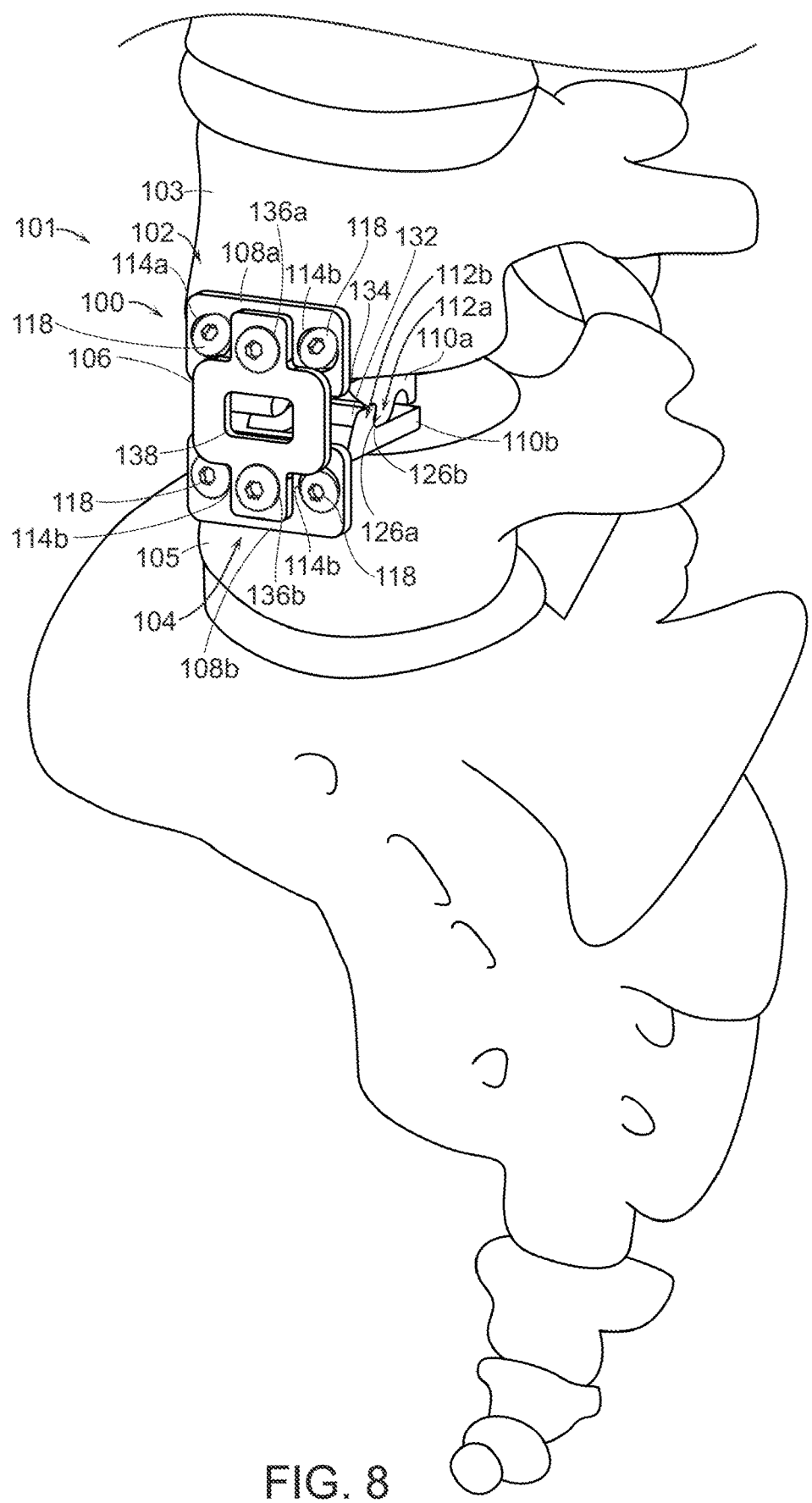
FIG. 8 is an isometric view of the spinal implant device of FIGS. 1A-2 during yet another stage of the spinal realignment and stabilization procedure in accordance with embodiments of the present technology.

FIG. 8 is an isometric view of the spinal implant device 100 during a subsequent stage of the spinal realignment and stabilization procedure in accordance with embodiments of the present technology. With the alignment system 202 is removed, the engagement features 112 of the vertebral supports 102, 104 act as a locking mechanism to maintain the vertebral alignment and restrict the first vertebral support 102 from slipping anteriorly relative to the second vertebral support 104. The engaged vertebral supports 102, 104 therefor provide at least temporary stabilization of the adjacent vertebrae 103, 105 before the anterior plate 106 is attached. As shown in FIG. 8, the anterior plate 106 is placed over the first and second vertebral supports 102 and 104 and permanently affixed thereto using screws 1 18 positioned through the attachment holes 136 of the plate 106 and the central plate attachment holes 116 of the vertebral supports 102, 104. In various embodiments, the screws 118 can be positioned at an angle to provide further bicortical fixation of the spinal implant device. Bone graft can then be packed into the window 138 of the anterior plate 106 as well as adjacent to and surrounding the vertebral supports 102, 104 (e.g., surrounding the engagement features 112 and the intervertebral portions 110) within the intradiscal space to induce spinal fusion postoperatively. In some embodiments, portions of the spinal plant device 100 (e.g., the anterior portions 108 of the vertebral supports 102, 104) have roughened surfaces to promote blood flow that will establish and promote cellular arthrodesis over time.

This spinal realignment and stabilization procedure corrects the forward displacement and sagittal rotation deformities associated with spondylolisthesis, distracts adjacent vertebrae to restore intervertebral height, and does so using an anterior approach and fixation from the anterior side. Thus, the spinal realignment and stabilization procedure is not expected to suffer from the same restrictions and complications associated with posterior approaches and posterior fixation, and benefit from the direct visualization and neural preservation provided by the anterior approach. The spinal implant device 100 also allows for bone graft insertion for long-term arthrodesis and boney fusion. Further, the spinal implant system 200 provides an integrated system that not only realigns vertebrae, but also stabilizes the vertebrae after realignment. The spinal implant system 200 is also modular in that the system 200 allows the spinal implant device 100, as well as the alignment system 202, to be assembled within the patient during a surgical procedure.

Examples

Several aspects of the present technology are set forth in the following examples.

1. A spinal implant system for patients with spinal malalignment, the system comprising:
a first vertebral support configured to be implanted at an anterior region of a first vertebra of a patient;
a second vertebral support configured to be implanted at an anterior region of a second vertebra of a patient, wherein the second vertebra is inferior to the first vertebra, and wherein the first and second vertebral supports are configured to extend into and interlock with each other within an interbody space between the first and second vertebrae when the first and second vertebral supports are aligned; and
an alignment system configured to operably couple to the first vertebral support and to the second vertebral support to adjust angular, vertical, and linear posterior alignment of the first and second vertebrae relative to each other, the alignment system comprising
a superior attachment component configured to releasably attach to the first vertebral support;
an inferior attachment component configured to releasably attach to the second vertebral support; and
a distraction assembly configured to be operably coupled to the superior attachment component and to the inferior attachment component, wherein the distraction assembly is configured to vertically displace the first vertebra from the second vertebra.

2. The spinal implant system of example 1 wherein:
the first vertebral support has a first anterior portion configured to be attached to the anterior region of the first vertebra, a first intervertebral portion configured to extend in a posterior direction from the first anterior portion, and a first engagement feature at the first intervertebral portion; and
the second vertebral support has a second anterior portion configured to be attached to the anterior region of the second vertebra, a second intervertebral portion configured to extend in the posterior direction from the second anterior portion, and a second engagement feature at the second intervertebral portion, wherein the first and second engagement features are configured to interlock within the interbody space between the first and second vertebrae.

3. The spinal implant system of example 2 wherein the first engagement feature includes a first ledge and the second engagement feature includes a second ledge, and wherein the first and second ledges are configured to engage each other when the first and second vertebral supports are aligned.

4. The spinal implant system of example 2 or 3 wherein:
the superior attachment component is configured to releasably attach to the first anterior portion of the first vertebral support and extend in an anterior direction from the first anterior support; and
the inferior attachment component is configured to releasably attach to the second anterior portion of the second vertebral support and extend in the anterior direction from the second anterior support.

5. The spinal implant system of example 4 wherein:
the superior attachment component comprises a superior shaft and a tube configured to receive the superior shaft, the tube having at least a first hole; and the inferior attachment component comprises an inferior shaft having a plurality of second holes extending along a length of the inferior shaft.

6. The spinal implant system of example 5 wherein the distraction assembly comprises:

a superior distraction component having a first plunger member configured to couple the superior distraction component to the tube by engaging the first hole; an inferior distraction component having a second plunger member configured to couple to the inferior shaft by engaging at least one of the second holes; and a distraction member extending between the superior distraction component and the inferior distraction component and configured to vertically separate the first vertebra from the second vertebra.

7. The spinal implant system of example 6 wherein the distraction member is a threaded shaft, and wherein rotating the threaded shaft separates the superior distraction component from the inferior distraction component along an axis extending through the threaded shaft.

8. The spinal implant system of any one of examples 5-7 wherein:

the tube of the superior attachment component includes internal threads; and the alignment assembly further comprises a linear translation driver having a threaded shaft configured to couple to the internal threads of the tube, wherein the linear translation is configured to linearly translate the first vertebra relative to the second vertebra by rotating the linear translation driver into further engagement with the internal threads of the tube.

9. The spinal implant system of any one of examples 1-5 wherein the distraction assembly comprises:

a superior distraction component configured to couple the superior attachment component;

an inferior distraction component configured to couple to the inferior attachment component; and a distraction member extending between the superior distraction component and the inferior distraction component and configured to vertically translate the first vertebra apart relative to the second vertebra.

10. The spinal implant system of any one of examples 1-7, further comprising a linear translation driver configured to couple to the superior support member or the inferior support member, wherein the linear translation driver is configured to linearly translate the first vertebra relative to the second vertebra.

11. The spinal implant system of any one of examples 1-10, further comprising an anterior reinforcement plate sized and shaped to fixedly attach to the first vertebral support and the second vertebral support.

12. The spinal implant system of any one of examples 1-11, further comprising: a plurality of first screws configured to attach the first vertebral support to the first vertebra, wherein the first screws extend through two separate portions of cortical bone of the first vertebra; and a plurality of second screws configured to attach the second vertebral support to the second vertebra, wherein the second screws extend through two separate portions of cortical bone of the second vertebra.

13. A modular spinal implant system for patients with spinal malalignment, the system comprising:

a first vertebral support having a first anterior portion configured to be attached to an anterior region of a first vertebra of a patient, a first intervertebral portion configured to extend in a posterior direction from the first anterior portion, and a first engagement feature at the first intervertebral portion;

a second vertebral support having a second anterior portion configured to be attached to an anterior region of a second vertebra of the patient adjacent to the first vertebra, a second intervertebral portion configured to extend in a posterior direction from the second anterior portion, and a second engagement feature at the second intervertebral portion, wherein the first and second engagement features are configured to interlock with each other within an interbody space between the first and second vertebrae when the first and second vertebral supports are aligned; and a reinforcement plate configured to connect to the first and second anterior portions to affix the first and second vertebral supports together.

14. The modular spinal implant system of example 13 wherein the first engagement feature includes a first angled ledge and the second engagement feature includes a second angled ledge, and wherein the first and second angled ledges are configured to interface with each other to lock the first and second vertebral supports together when the first and second vertebral supports are aligned.

15. The modular spinal implant system of example 13 or 14, further comprising: at least one first shaft configured to attach the first vertebral support to the first vertebra, wherein the at least one first shaft extends through two separate portions of cortical bone of the first vertebra; and at least a second shaft configured to attach the second vertebral support to the second vertebra, wherein the at least one second shaft extends through two separate portions of cortical bone of the second vertebra.

16. The modular spinal implant system of any one of examples 13-15, further comprising an alignment system configured to be releasably coupled to the first and second vertebral supports, wherein the alignment system comprises:

a superior attachment component configured to releasably attach to the first anterior portion of the first vertebral support;

an inferior attachment component configured to releasably attach to the second anterior portion of the second vertebral support, wherein applying torque to at least one of the superior attachment component and the inferior attachment component is configured to correct sagittal rotation deformities of the first and second vertebrae relative to each other;

a distraction assembly configured to be coupled to the superior and inferior attachment components, wherein the distraction assembly is movable to vertically displace the first vertebra from the second vertebra; and a linear alignment member configured to be coupled to at least one of the superior attachment component and the inferior attachment component, wherein the linear alignment member is movable to linearly align the first and second vertebrae.

17. The modular spinal implant system of example 16 wherein the alignment system extends in an anterior direction with respect to the first and second vertebral supports when the alignment system is coupled to the first and second vertebral supports.

18. The modular spinal implant system of example 16 or 17 wherein the distraction assembly comprises a distraction component extending between the superior and inferior attachment components, and wherein manipulating the distraction component is configured to vertically separate the first and second vertebral supports.

19. The modular spinal implant system of any one of examples 13-18 wherein at least one of the anterior plate, the first vertebral support, and the second vertebral support comprise at least one window configured to receive bone graft to facilitate arthrodesis between the first and second vertebrae.

20. A method for implanting a spinal implant device to treat spinal malalignment, the method comprising:

affixing a first vertebral support to an anterior portion of a first vertebra of a patient; affixing a second vertebral support to an anterior portion of a second vertebra of the patient adjacent to the first vertebra;

releasably coupling an alignment system to the first and second vertebral supports; applying torque to the alignment system to angularly align the first vertebra with the second vertebra;

manipulating a distraction assembly of the alignment system to vertically translate the first and second vertebrae; and manipulating a linear alignment member to translate the first vertebra in a posterior direction relative to the second vertebra, wherein the first and second vertebral supports interlock with each other when the first and second vertebra are aligned.

21. The method of example 20 wherein affixing the first vertebral support to the anterior portion of the first vertebra comprises affixing a screw through an anterior portion of the first vertebral support and through two spaced apart portions of cortical bone of the first vertebra.

22. The method of example 20 or 21, further comprising: decoupling the alignment system from the first and second vertebral supports; and fixedly attaching an anterior reinforcement plate to anterior portions of the first and second vertebral supports while the first and second vertebral supports are interlocked.

23. The method of any one of examples 20-22, further comprising accessing the first and second vertebrae from an anterior side via an incision in a patient.

24. The method of any one of examples 20-23, further comprising releasing, from an anterior position relative to the first and second vertebrae, native structures proximate to the first and second vertebrae holding malalignment of the first and second vertebrae in place.

25. The method of any one of examples 20-24, further comprising removing abnormal disc space between the first and second vertebrae from an anterior position relative to the first and second vertebrae.

26. The method of any one of examples 20-25 wherein releasably coupling the alignment system to the first and second vertebrae comprises:

releasably coupling a first attachment component to the first vertebral support;

releasably coupled a second attachment component to the second vertebral support, wherein the first and second attachment components extend in an anterior direction from the first and second vertebral supports.

27. The method of example 26 wherein applying torque to the alignment system to angularly align the first and second vertebrae comprises applying torque to the first attachment component.

28. The method of example 26 or 27 wherein manipulating the distraction assembly of the alignment system to vertically translate the first and second vertebrae comprises rotating a screw extending between and operably coupled to the first and second attachment components to distract disc space between the first and second vertebrae.

29. The method of any one of examples 26-28 wherein manipulating the linear alignment member to translate the first vertebra in the posterior direction comprises applying torque to the linear alignment member as the linearly alignment member is engaged with the first attachment feature such that the first attachment feature drives the first vertebral support in the posterior direction.

30. The method of any one of examples 20-29, further comprising manipulating the distraction assembly of the alignment system to vertically translate the first and second vertebrae closer together when the first and second vertebrae are aligned to interlock the first and second vertebral supports.

31. The method of any one of examples 20-30 wherein affixing the first and second vertebral supports to anterior portions of the first and second vertebrae, respectively, comprises:

affixing a first anterior portion of the first vertebral support to the anterior portion of the first vertebrae such that a first intervertebral portion extends in a posterior direction from the first anterior portion into intervertebral space between the first and second vertebrae; and affixing a second anterior portion of the second vertebral support to the anterior portion of the second vertebrae such that a second intervertebral portion extends in a posterior direction from the second anterior portion into interbody space between the first and second vertebrae.

32. The method of any one of examples 20-31 wherein affixing the first and second vertebral supports to anterior portions of the first and second vertebrae, respectively, comprises:

affixing the first vertebral support to the first vertebra positioned in a lumbar spine of the patient, wherein the first vertebra is anteriorly misaligned with the second vertebra.

33. The method of any one of examples 20-32, further comprising inserting bone graft around the first and second vertebral supports for long-term arthrodesis and boney fusion of the first and second vertebrae.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method for implanting a spinal implant device to treat spinal malalignment between a first vertebra and a second vertebra, the method comprising:
    affixing a first vertebral support to an anterior portion of the first vertebra of a patient such that a first intervertebral portion of the first vertebral support extends within a space between the first vertebra and the second vertebra;
    affixing a second vertebral support to an anterior portion of the second vertebra of the patient adjacent to the first vertebra such that a second intervertebral portion extends within the space;
    releasably coupling an alignment system to the first and second vertebral supports;
    applying torque to the alignment system to angularly align the first vertebra with the second vertebra;
    manipulating a distraction assembly of the alignment system to vertically translate the first and second vertebrae; and
    manipulating a linear alignment member to translate the first vertebra in a posterior direction relative to the second vertebra while the first intervertebral portion and the second intervertebral portion are uncoupled, wherein the first intervertebral portion and the second intervertebral portion interlock with each other when the first and second vertebra are aligned.

2. The method of claim 1, wherein affixing the first vertebral support to the anterior portion of the first vertebra comprises affixing a screw through an anterior portion of the first vertebral support and through two spaced apart portions of cortical bone of the first vertebra.

3. The method of claim 1, further comprising:
    decoupling the alignment system from the first and second vertebral supports; and
    fixedly attaching an anterior reinforcement plate to anterior portions of the first and second vertebral supports while the first and second vertebral supports are interlocked.

4. The method of claim 1, further comprising accessing the first and second vertebrae from an anterior side via an incision in a patient.

5. The method of claim 1, further comprising releasing, from an anterior position relative to the first and second vertebrae, native structures proximate to the first and second vertebrae holding malalignment of the first and second vertebrae in place.

6. The method of claim 1, further comprising removing abnormal disc space between the first and second vertebrae from an anterior position relative to the first and second vertebrae.

7. The method of claim 1, wherein releasably coupling the alignment system to the first and second vertebrae comprises:
    releasably coupling a first attachment component to the first vertebral support;
    releasably coupled a second attachment component to the second vertebral support, wherein the first and second attachment components extend in an anterior direction from the first and second vertebral supports.

8. The method of claim 7, wherein applying torque to the alignment system to angularly align the first and second vertebrae comprises applying torque to the first attachment component.

9. The method of claim 7, wherein manipulating the distraction assembly of the alignment system to vertically translate the first and second vertebrae comprises rotating a screw extending between and operably coupled to the first and second attachment components to distract disc space between the first and second vertebrae.

10. The method of claim 7, wherein manipulating the linear alignment member to translate the first vertebra in the posterior direction comprises applying torque to the linear alignment member as the linearly alignment member is engaged with the first attachment feature such that the first attachment feature drives the first vertebral support in the posterior direction.

11. The method of claim 7, further comprising manipulating the distraction assembly of the alignment system to vertically translate the first and second vertebrae closer together when the first and second vertebrae are aligned to interlock the first and second vertebral supports.

12. The method of claim 7, wherein affixing the first and second vertebral supports to anterior portions of the first and second vertebrae, respectively, comprises:
    affixing a first anterior portion of the first vertebral support to the anterior portion of the first vertebrae such that a first intervertebral portion extends in a posterior direction from the first anterior portion into intervertebral space between the first and second vertebrae; and
    affixing a second anterior portion of the second vertebral support to the anterior portion of the second vertebrae such that a second intervertebral portion extends in a posterior direction from the second anterior portion into interbody space between the first and second vertebrae.

13. The method of claim 1, wherein affixing the first and second vertebral supports to anterior portions of the first and second vertebrae, respectively, comprises:
    affixing the first vertebral support to the first vertebra positioned in a lumbar spine of the patient, wherein the first vertebra is anteriorly misaligned with the second vertebra.

14. The method of claim 1, further comprising inserting bone graft around the first and second vertebral supports for long-term arthrodesis and boney fusion of the first and second vertebrae.

* * * * *